US011123129B2

(12) United States Patent
Boudreaux

(10) Patent No.: US 11,123,129 B2
(45) Date of Patent: Sep. 21, 2021

(54) DUAL STAGE ENERGY ACTIVATION FOR ELECTROSURGICAL SHEARS

(71) Applicant: ETHICON LLC, Guaynabo, PR (US)

(72) Inventor: Chad P. Boudreaux, Cincinnati, OH (US)

(73) Assignee: Cilag GmbH International, Zug (CH)

( * ) Notice: Subject to any disclaimer, the term of this patent is extended or adjusted under 35 U.S.C. 154(b) by 411 days.

(21) Appl. No.: 15/989,452

(22) Filed: May 25, 2018

(65) Prior Publication Data

US 2019/0357967 A1  Nov. 28, 2019

(51) Int. Cl.
*A61B 18/14* (2006.01)
*A61B 18/12* (2006.01)
*A61B 18/00* (2006.01)

(52) U.S. Cl.
CPC ...... *A61B 18/1442* (2013.01); *A61B 18/1206* (2013.01); *A61B 2018/0063* (2013.01); *A61B 2018/00601* (2013.01); *A61B 2018/126* (2013.01); *A61B 2018/1455* (2013.01)

(58) Field of Classification Search
CPC ............ A61B 18/1206; A61B 18/1442; A61B 18/1445; A61B 2018/00601; A61B 2018/00607; A61B 2018/0063; A61B 2018/00916; A61B 2018/126; A61B 2018/1455; A61B 2018/00946
See application file for complete search history.

(56) References Cited

U.S. PATENT DOCUMENTS

| | | |
|---|---|---|
| 6,500,176 B1 | 12/2002 | Truckai et al. |
| 7,112,201 B2 | 9/2006 | Truckai et al. |
| 7,125,409 B2 | 10/2006 | Truckai et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |

(Continued)

FOREIGN PATENT DOCUMENTS

WO  WO 2016/168567 A2  10/2016

OTHER PUBLICATIONS

U.S. Appl. No. 15/989,424, entitled "Method and Apparatus for Open Electrosurgical Shears," filed May 25, 2018.

(Continued)

*Primary Examiner* — Michael F Peffley
(74) *Attorney, Agent, or Firm* — Frost Brown Todd LLC

(57) ABSTRACT

A surgical instrument includes an end effector, a handle assembly, and an electrode activation assembly. The end effector includes a first jaw, a second jaw, a knife, and an electrode assembly. The handle assembly includes a housing, and an arm. The arm can pivot the second jaw between the open position and the closed position. The arm can pivot relative to the housing between a first position, a second position, and a third position. The electrode activation assembly includes an activation button associated with the handle assembly, a resilient body, and a detent associated with either the housing or the arm. The activation button can activate the electrode assembly in response to the arm pivoting to the third position. The resilient body includes a first cam feature. The detent can engage the first cam feature as the arm pivots between the first position and the second position.

20 Claims, 24 Drawing Sheets

(56) References Cited

U.S. PATENT DOCUMENTS

| | | | |
|---|---|---|---|
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,381,209 B2 | 6/2008 | Truckai et al. | |
| 7,628,791 B2 * | 12/2009 | Garrison | A61B 18/1445 606/51 |
| 7,909,823 B2 * | 3/2011 | Moses | A61B 17/3201 606/51 |
| 7,922,718 B2 * | 4/2011 | Moses | A61B 18/1442 606/51 |
| 8,939,974 B2 | 1/2015 | Boudreaux et al. | |
| 9,089,327 B2 | 7/2015 | Worrell et al. | |
| 9,161,803 B2 | 10/2015 | Yates et al. | |
| 9,402,682 B2 | 8/2016 | Worrell et al. | |
| 9,545,253 B2 | 1/2017 | Worrell et al. | |
| 9,610,114 B2 | 4/2017 | Baxter, III et al. | |
| 9,877,720 B2 | 1/2018 | Worrell et al. | |
| 2016/0175029 A1 | 6/2016 | Witt et al. | |
| 2016/0175030 A1 * | 6/2016 | Boudreaux | A61B 18/1442 606/42 |
| 2017/0281211 A1 * | 10/2017 | Strobl | A61B 18/1445 |

OTHER PUBLICATIONS

U.S. Appl. No. 15/989,430, entitled "Electrosurgical Shears with Knife Lock and Clamp-Actuated Switch," filed May 25, 2018.
U.S. Appl. No. 15/989,433, entitled "Knife Drive Assembly for Electrosurgical Shears," filed May 25, 2018.
U.S. Appl. No. 15/989,438, entitled "Knife Auto-Return Assembly for Electrosurgical Shears," filed May 25, 2018.
U.S. Appl. No. 15/989,442, entitled "Compound Screw Knife Drive for Electrosurgical Shears," filed May 25, 2018.
U.S. Appl. No. 15/989,448, entitled "Firing and Lockout Assembly for Knife for Electrosurgical Shears," filed May 25, 2018.
U.S. Appl. No. 15/989,455, entitled "Latching Clamp Arm for Electrosurgical Shears," filed May 25, 2018.
International Search Report and Written Opinion dated Sep. 6, 2019 for Application No. PCT/IB2019/053693, 10 pgs.

* cited by examiner

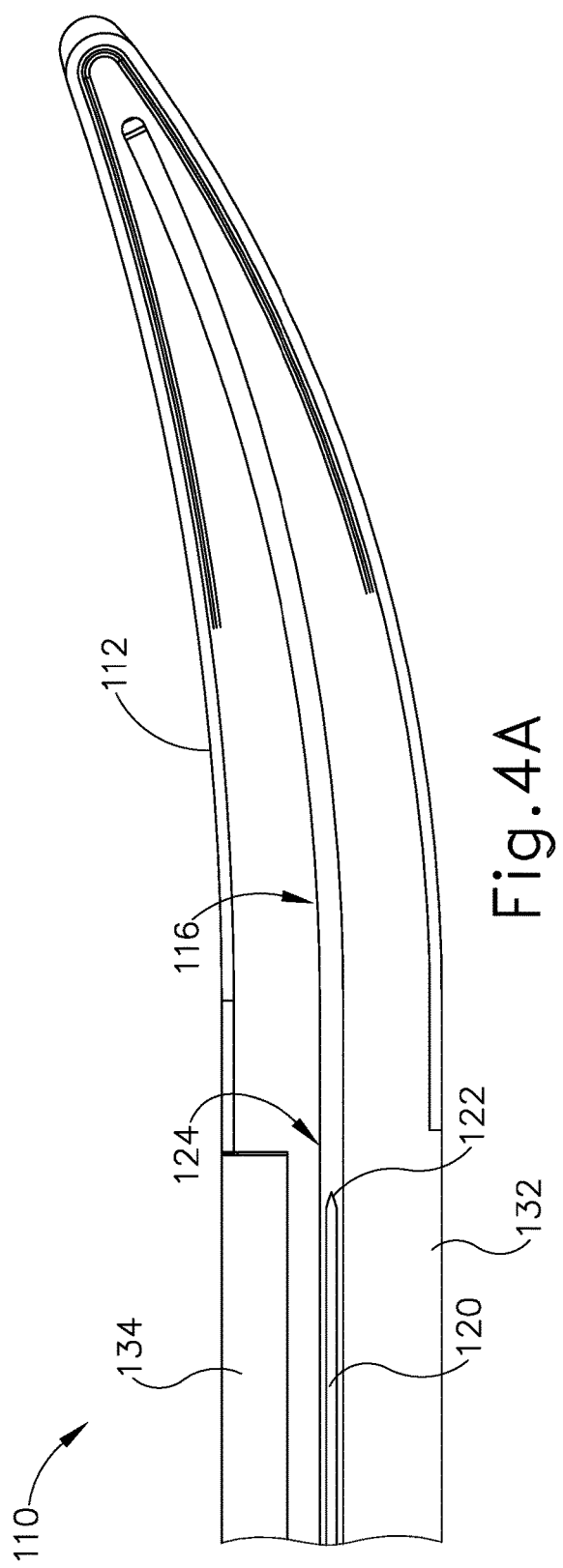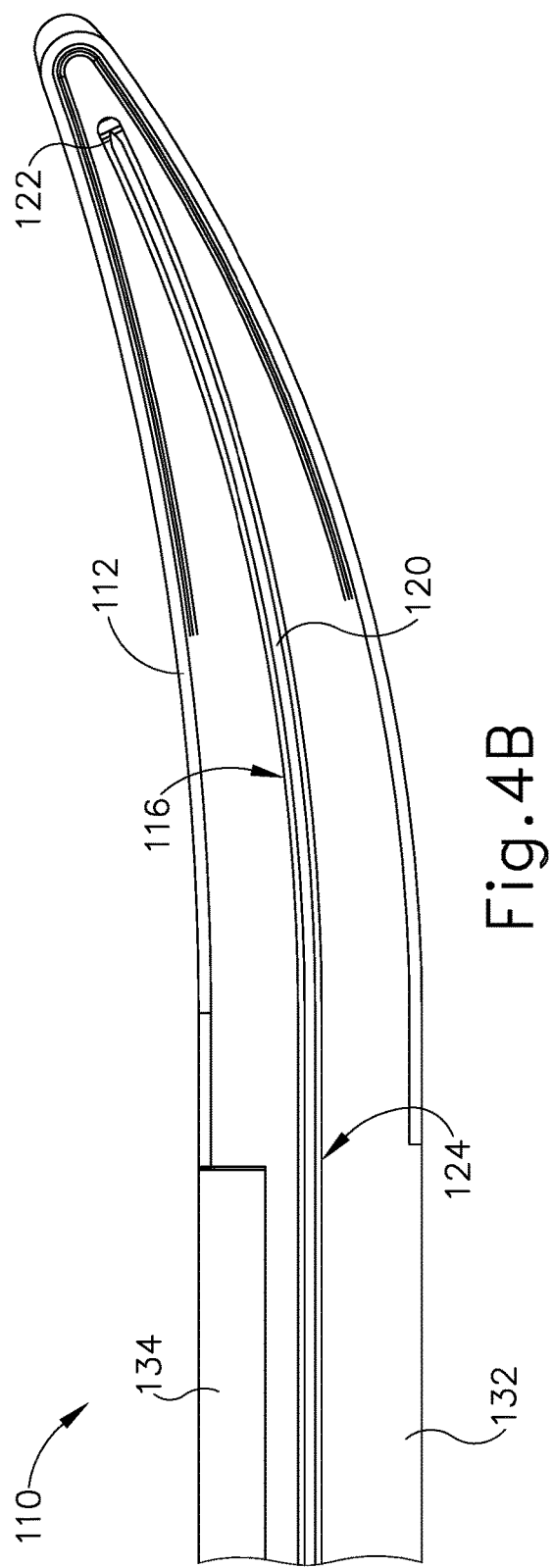

DUAL STAGE ENERGY ACTIVATION FOR ELECTROSURGICAL SHEARS

BACKGROUND

A variety of surgical instruments include one or more elements that transmit RF energy to tissue (e.g., to coagulate or seal the tissue). Some such instruments comprise a pair of jaws that open and close on tissue, with conductive tissue contact surfaces that are operable to weld tissue clamped between the jaws. In open surgical settings, some such instruments may be in the form of forceps having a scissor grip.

In addition to having RF energy transmission elements, some surgical instruments also include a translating tissue cutting element. An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pat. No. 8,939,974, entitled "Surgical Instrument Comprising First and Second Drive Systems Actuatable by a Common Trigger Mechanism," issued Jan. 27, 2015, the disclosure of which is incorporated by reference herein; U.S. Pat. No. 9,161,803, entitled "Motor Driven Electrosurgical Device with Mechanical and Electrical Feedback," issued Oct. 20, 2015, the disclosure of which is incorporated by reference herein; U.S. Pat. No. 9,877,720, entitled "Control Features for Articulating Surgical Device," issued Jan. 30, 2018, the disclosure of which is incorporated by reference herein; U.S. Pat. No. 9,402,682, entitled "Articulation Joint Features for Articulating Surgical Device," issued Aug. 2, 2016, the disclosure of which is incorporated by reference herein; U.S. Pat. No. 9,089,327, entitled "Surgical Instrument with Multi-Phase Trigger Bias," issued Jul. 28, 2015, the disclosure of which is incorporated by reference herein; and U.S. Pat. No. 9,545,253, entitled "Surgical Instrument with Contained Dual Helix Actuator Assembly," issued Jan. 17, 2017, the disclosure of which is incorporated by reference herein.

Some versions of electrosurgical instruments that are operable to sever tissue may be selectively used in at least two modes. One such mode may include both severing tissue and coagulating tissue. Another such mode may include just coagulating tissue without also severing the tissue. Yet another mode may include the use of jaws to grasp and manipulate tissue without also coagulating and/or severing the tissue. When an instrument includes grasping jaws and tissue severing capabilities, the instrument may also include a feature that ensures full closure of the jaws before the tissue is severed and/or before the electrodes are activated.

While various kinds of surgical instrument have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 4A depicts a cross-sectional view of the end effector of FIG. 1, taken along line 4-4 of FIG. 1, where the translating knife of FIG. 2 is in the proximal position;

FIG. 4B depicts a cross-sectional view of the end effector of FIG. 1, taken along line 4-4 of FIG. 1, where the translating knife of FIG. 2 is in the distal position;

DETAILED DESCRIPTION

Figure 1:
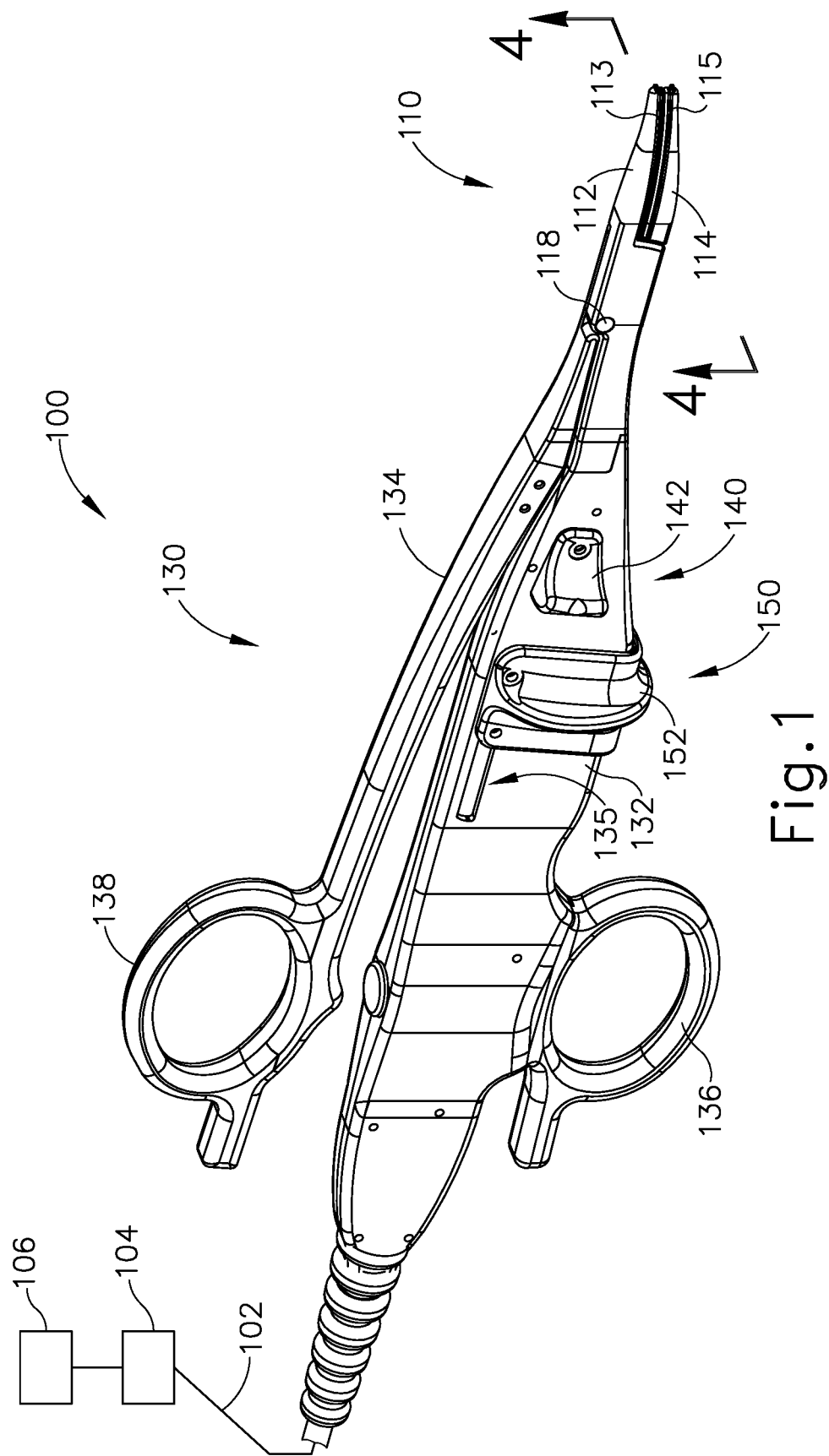
FIG. 1 depicts a perspective view of an exemplary electrosurgical forceps instrument, where an end effector is in a closed position, where a resilient arm is in a relaxed position.
Figure 2:
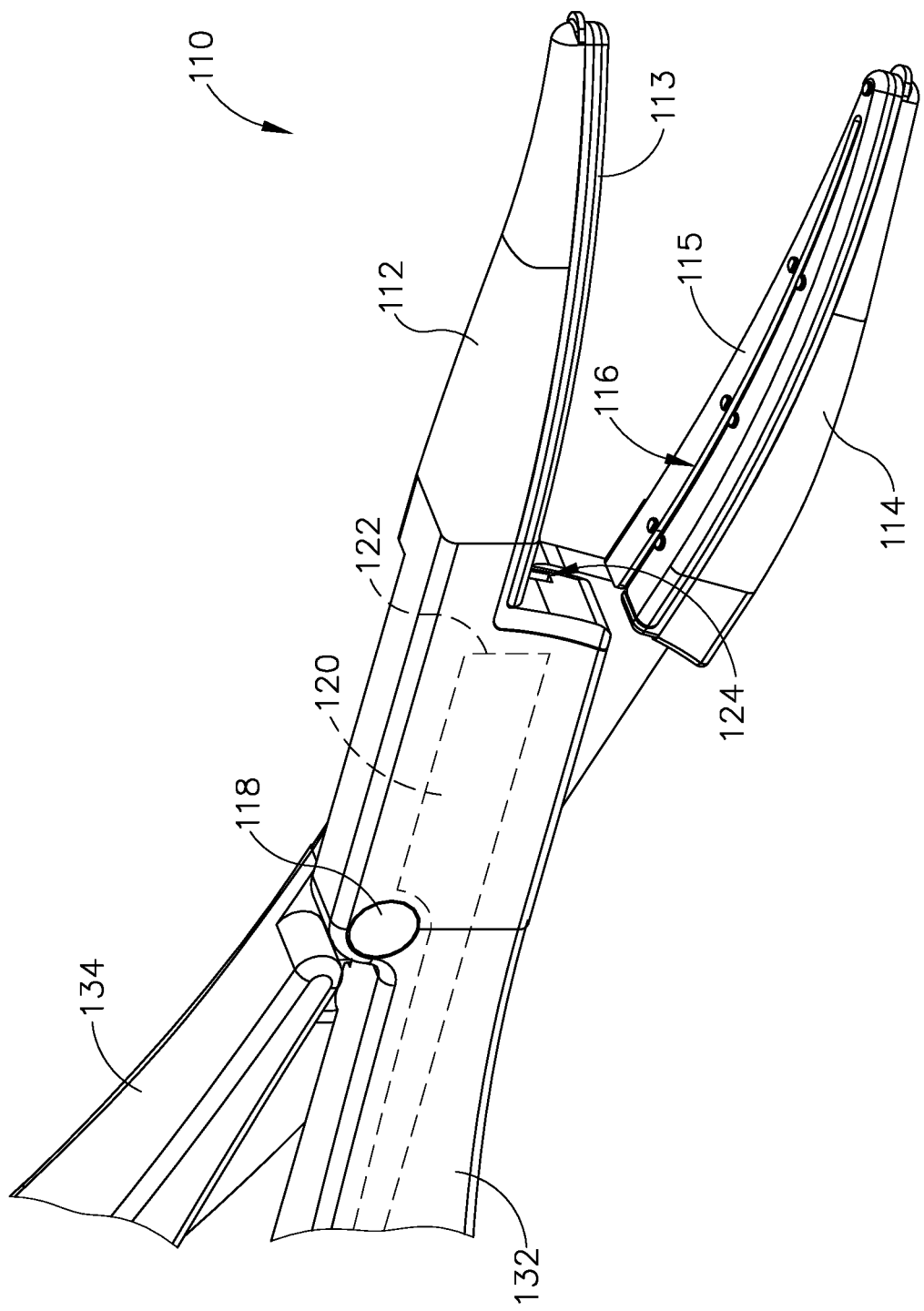
FIG. 2 depicts a perspective view of the end effector of FIG. 1 in an opened position, where a translating knife is in a proximal position.

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Electrosurgical Forceps

As previously noted, an electrosurgical instrument may include a set of jaws, with at least one of the jaws being pivotable relative to the other jaw to selectively compress tissue between the jaws. Once the tissue is compressed, electrodes in the jaws may be activated with bipolar RF energy to seal the tissue. In some instances, a cutting feature is operable to sever tissue that is clamped between the jaws. For instance, the cutting feature may be actuated before or after the RF energy has sealed the tissue. Various references that are cited herein relate to electrosurgical instruments where the jaws are part of an end effector at the distal end of an elongate shaft, such that the end effector and the shaft may be inserted through a port (e.g., a trocar) to reach a site within a patient during a minimally invasive endoscopic surgical procedure. A handle assembly may be positioned at the proximal end of the shaft for manipulating the end effector. Such a handle assembly may have a pistol grip configuration or some other configuration.

In some instances, it may be desirable to provide an electrosurgical instrument that does not have an elongate shaft or handle assembly similar to those described in the various references cited herein. In particular, it may be desirable to provide an electrosurgical instrument that is configured similar to a forceps device, with a scissor grip. Such instruments may be used in a variety of medical procedures. Various examples of electrosurgical shears/forceps devices are disclosed in U.S. Pat. No. 9,610,144, entitled "Electrosurgical Hand Shears," filed Jan. 29, 2013, the disclosure of which is incorporated by reference herein. Various other examples of electrosurgical forceps instruments will be described in greater detail below; while other examples will be apparent to those of ordinary skill in the art in view of the teachings herein.

FIGS. 1-4B show an exemplary electrosurgical forceps instrument (100). Instrument (100) includes a handle assembly (130) extending distally into an end effector (110). As will be described in greater detail below, instrument (100) may be used to grasp, seal, and sever tissue captured by end effector (110).

End effector (110) includes a first jaw (112) having a first electrode (113), a second jaw (114) having a second electrode (115), and a knife (120) configured to translate through the first jaw (112) and the second jaw (114). First jaw (112) and second jaw (114) are pivotably coupled with each other via pivot pin (118). First jaw (112) and second jaw (114) may pivot between an open position (FIG. 2) and a closed position (FIG. 1) in order to grasp tissue. First and second electrodes (113, 115) are positioned on respective jaws (112, 114) such that electrodes (113, 115) face each other when jaws (112, 114) are pivoted into the closed position. Additionally, each electrode (113, 115) is U-shaped in the present example, with the bend of the U-shape located near the distal end of each respective jaw (112, 114), such that each electrode (113, 115) includes two longitudinally extending, laterally spaced-apart legs extending along the length of each respective jaw (112, 114). Laterally spaced-apart legs of each electrode (113, 115) and corresponding portions of jaws (112, 114) define an elongate slot (116). Elongate slot (116) is dimensioned to slidably receive knife (120) such that knife may translate from a proximal position (FIG. 4A) to a distal position (FIG. 4B). Knife (120) includes a distal cutting edge (122) configured to sever tissue captured between jaws (112, 114) in the closed position.

A cable (102) extends proximally from handle assembly (130). Cable (102) is coupled with a control unit (104), which is further coupled with a power source (106). Power source (106) may power control unit (104). Control unit (104) is operable to provide RF power to electrodes (113, 115) of jaws (112, 114), to thereby seal tissue suitably captured between jaws (112, 114).

Handle assembly (130) includes a housing (132), and a resilient arm (134). Housing (132) contains an electrode activation assembly (140) and a firing assembly (150). Housing (132) and resilient arm (134) are pivotably coupled with each other via pivot pin (118). Housing (132) extends distally into first jaw (112), while resilient arm (134) extends distally into second jaw (114). Housing (132) defines a knife pathway (124) that slidably houses knife (120). Housing (132) includes a finger ring (136) while resilient arm (134) terminates proximally into a thumb ring (138). Therefore, the operator may grasp instrument (100) in a scissor grip fashion and pivot resilient arm (134) relative to housing (132) via rings (136, 138) in order to open and close jaws (112, 114).

Resilient arm (134) is sufficiently resilient that arm (134) may flex from a relaxed position (FIG. 3B) to a flexed position (FIG. 3C) in response to pivoting arm (134) further toward housing (132) when jaws (112, 114) are already in the closed position. Resilient arm (134) is biased toward the relaxed position. Further pivoting of resilient arm (134) into the flexed position may result in greater closure forces between jaws (112, 114) as compared to pivoting jaws (112, 114) into the closed position while arm (134) is in the relaxed position. Resilient arm (134) may be suitably resilient such that when resilient arm (134) is pivoted into the flexed position, the closure force between jaws (112, 114) is sufficient such that electrodes (113, 115) may properly seal tissue grasped between jaws (112, 114). Additionally, the resilient nature of arm may limit the amount of closure force between jaws (112, 114) such that jaws (112, 114) may not compress tissue too much, resulting in inadvertent tissue damage. When the operator no longer desires to compress tissue between jaws (112, 114) to properly seal clamped tissue, the operator may reduce the amount of closure force applied to resilient arm (134) such that arm (134) returns to the relaxed state.

Housing (132) slidingly supports an RF trigger (142) of electrode activation assembly (140). RF trigger (142) is in communication with control unit (104). RF trigger (142) may be pressed or actuated to command control unit (104) to supply RF energy to electrodes (113, 115) of end effector (110). RF trigger (142) may electrically couple with control unit (104) through any suitable components known to a person having ordinary skill in the art in view of the teachings herein.

As will be described in greater detail below, firing assembly (150) is configured to actuate knife (120) within jaws (112, 114) from a proximal position to a distal position in order to sever tissue captured between jaws (112, 114). Previous firing assemblies for electrosurgical forceps may have had a trigger that was a lever arm configured to rotate relative to a handle assembly to actuate a knife. The lever arm may have extended away from the handle assembly in order to provide a mechanical advantage for actuating knife within jaws (112, 114). However, when lever arm extends away from handle assembly, it may become difficult rotate lever arm when instrument is flipped such that thumb ring becomes finger rings and vice versa. In such instances when instrument is flipped, the lever arm may no longer associate with the index/middle finger for actuating the lever arm.

Therefore, it may be desirable to have a compact firing assembly with a trigger close to the center of housing such that it is easy to actuate firing assembly with the same finger(s), even when instrument is flipped. Firing assembly (150) of the current example includes a knife trigger (152) slidably coupled with housing (132) via a slot (135). Trigger (152) is close to the center of housing (132) such that trigger (152) may be easily accessed regardless if instrument (100) is flipped around. Trigger (152) may actuate relative to housing (132) in order to actuate a knife (120) of end effector (110). In particular, proximal translation of trigger (152) results in distal translation of knife (120), while distal translation of trigger (152) results in proximal translation of knife (120). Trigger (152) may be biased toward the distal position such that knife (120) is biased toward the proximal position.

Trigger (152) may be coupled with knife (120) through any suitably firing mechanism assembly as would be apparent to one having ordinary skill in the art in view of the teachings herein. It should be understood that trigger (152) may be selectively actuated at any suitable time the operator desires. For instance, the operator may grasp tissue by pivoting jaws (112, 114) to the closed position, wait a desired amount of time, and fire trigger (152) to actuate knife (120) and sever tissue. Alternative, the operator may grasp tissue by pivoting jaws (112, 114), release tissue if jaws (112, 114) are not satisfactorily grasping tissue, re-grasp tissue, and then fire trigger (152) to actuate knife (120) and sever tissue.

Figure 3A:
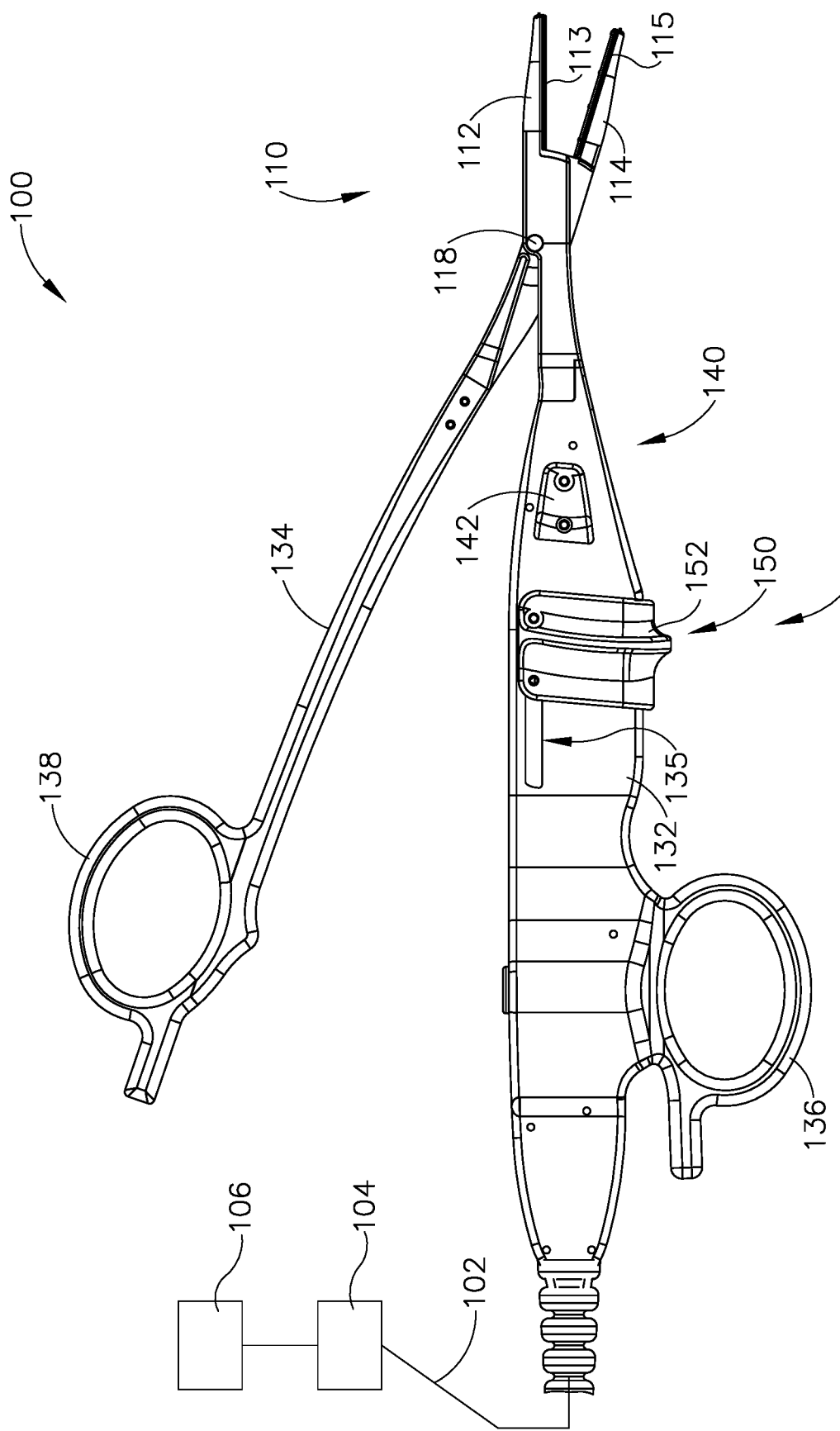
FIG. 3A depicts a side elevational view of the electrosurgical forceps instrument of FIG. 1, where the end effector is in the opened position, where the resilient arm is in the relaxed position, and where the translating knife of FIG. 2 is in the proximal position.

FIGS. 3A-4B show an exemplary operation of instrument (100). FIG. 3A shows jaws (112, 114) of end effector (110) in the opened position. Therefore, resilient arm (134) is pivoted away from housing (132). As shown in FIG. 3B, when the operator desires to initially grasp and manipulate tissue, the operator may pivot resilient arm (134) toward housing (132) such that jaws (112, 114) are pivoted toward the closed position while resilient arm (134) remains in the relaxed position. With jaws (112, 114) pivoted toward the closed position, the operator may manipulate tissue grasped by jaws (112, 114). It should be understood that the closure forces imparted on tissue by jaws (112, 114) at this point may not be sufficient enough for suitable sealing of tissue via RF energy provided by electrodes (113, 115).

Figure 3B:
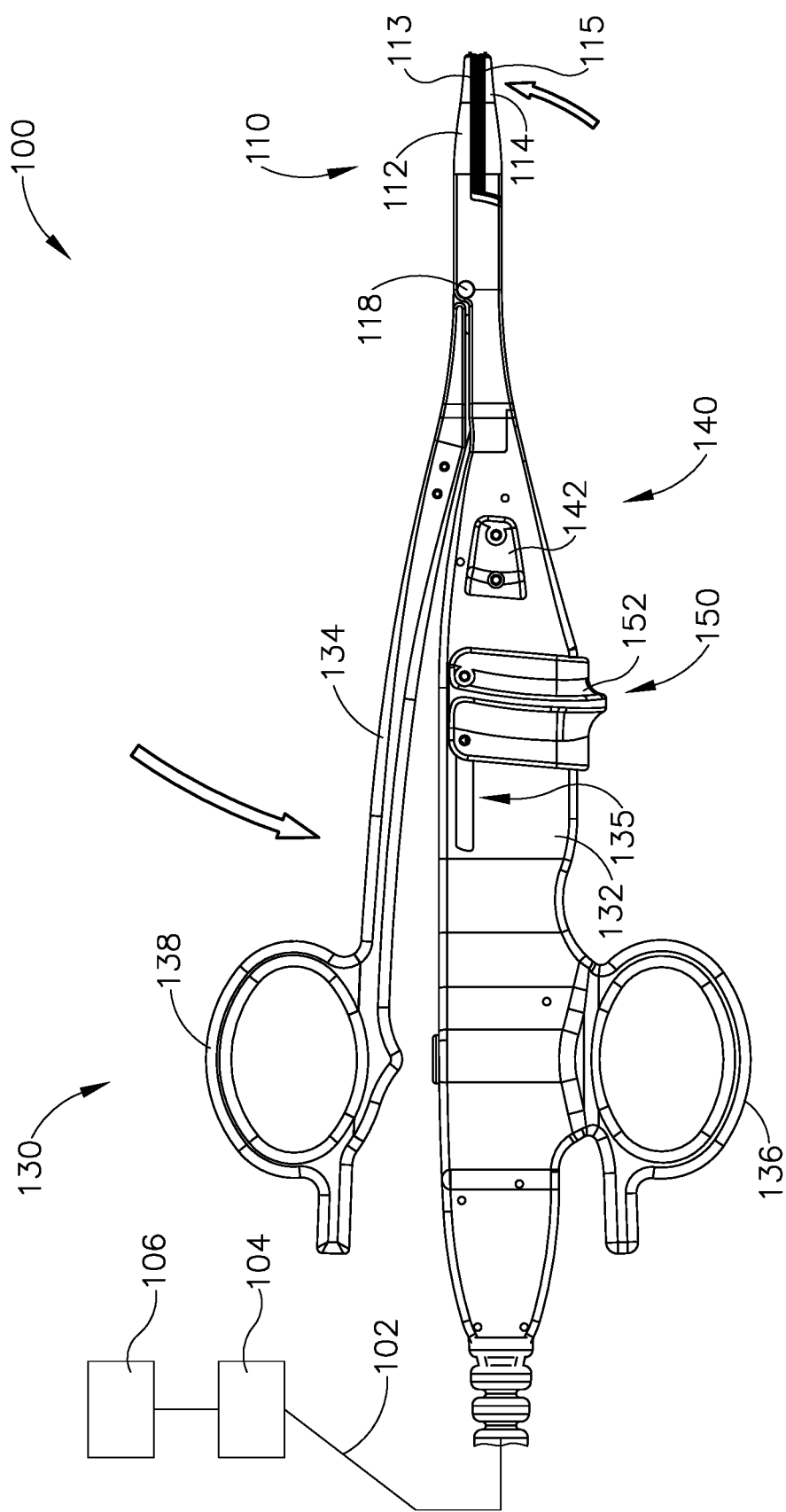
FIG. 3B depicts a side elevational view of the electrosurgical forceps instrument of FIG. 1, where the end effector is in the closed position, where the resilient arm is in the relaxed position, and where the translating knife of FIG. 2 is in the proximal position.
Figure 3C:
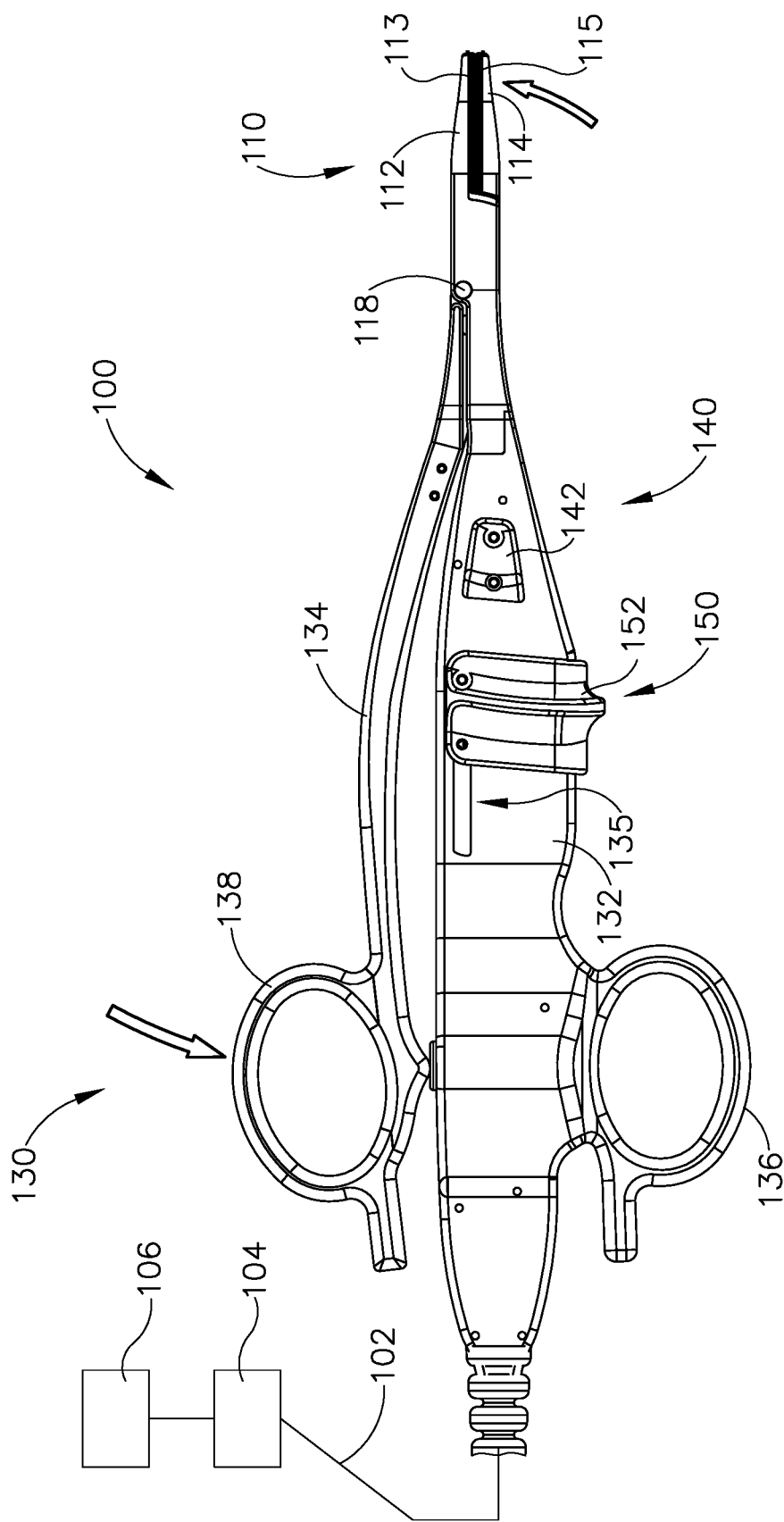
FIG. 3C depicts a side elevational view of the electrosurgical forceps instrument of FIG. 1, where the end effector is in the closed position, where the resilient arm is in a flexed position, and where the translating knife of FIG. 2 is in the proximal position.
Figure 3D:
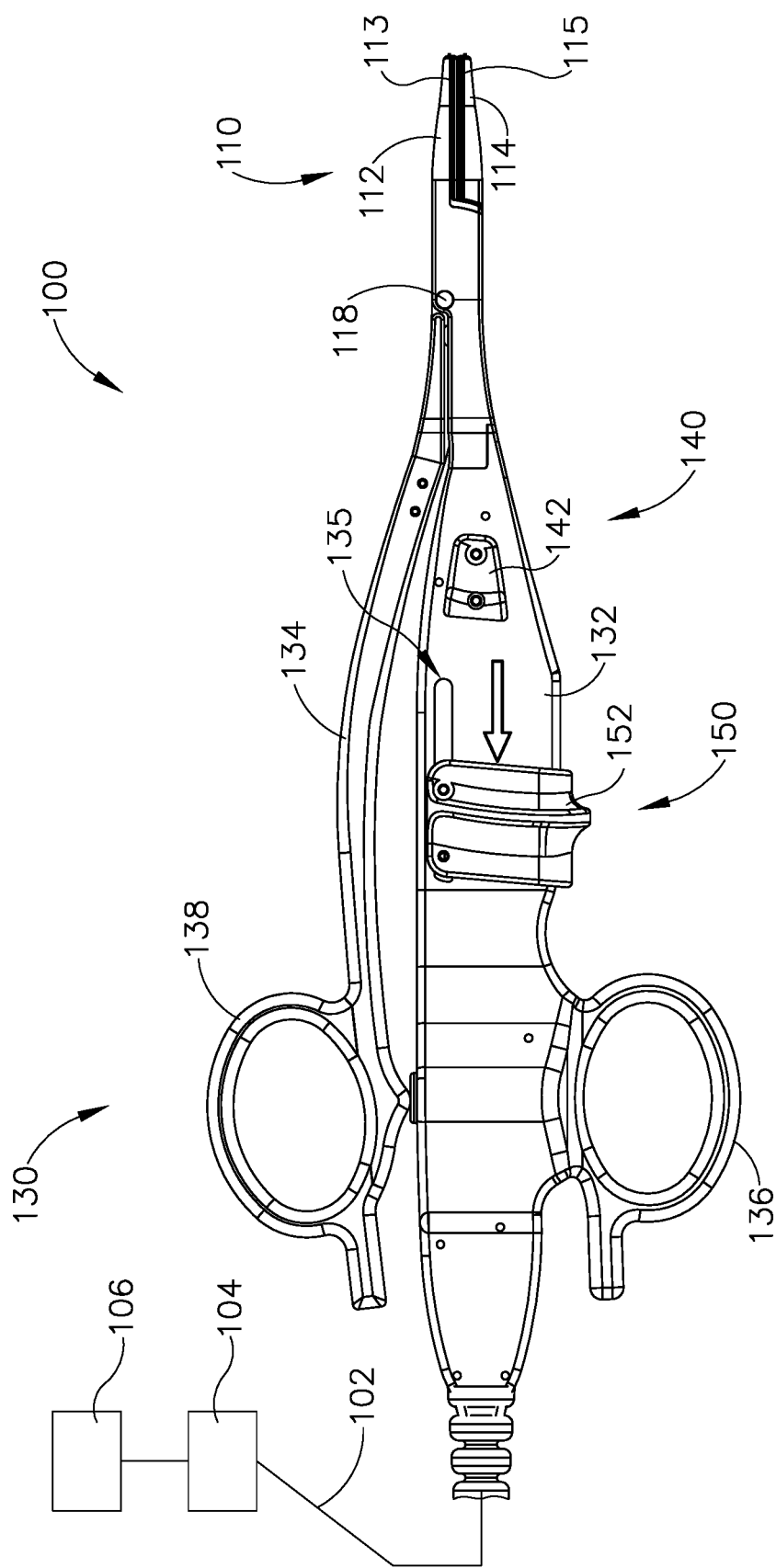
FIG. 3D depicts a side elevational view of the electrosurgical forceps instrument of FIG. 1, where the end effector is in the closed position, where the resilient arm is in the flexed position, and where the translating knife of FIG. 2 is in a distal position.

Next, as shown in FIG. 3C, if the operator desires to apply RF energy to grasped tissue, the operator may further pivot resilient arm (134) toward housing (132) such that resilient arm bends to the flexed position. As this point, the closure forces imparted on tissue by jaws (112, 114) is sufficient for proper sealing. The operator may then actuate RF trigger (142) such that electrodes (113, 115) provide RF energy to grasped tissue. Next, as shown between FIGS. 3C-3D and 4A-4B, the operator may desire to sever tissue captured between jaws (112, 114). Therefore, the operator may actuate trigger (152) proximally as shown between FIGS. 3C-3D such that knife (120) actuates distally as shown between FIGS. 4A-4B. Cutting edge (122) may sever tissue captures between jaws (112, 114) as knife (120) actuates distally through elongate slot (116).

While in the current example, the operator applies RF energy to grasped tissue and then subsequently severs the tissue, the operator may alternatively sever grasped tissue first, then apply RF energy to the tissue as would be apparent to one of ordinary skill in the art in accordance with the teachings herein. Alternatively, the operator may only seal grasped tissue by applying RF energy, without severing the tissue, as would be apparent to one of ordinary skill in the art in accordance with the teachings herein. Alternately, the operator may only sever grasped tissue, without sealing the tissue, as would be apparent to one of ordinary skill in the art in accordance with the teachings herein. Alternatively, the operator may just grasp tissue, without severing or sealing the tissue, as would be apparent to one of ordinary skill in the art in accordance with the teachings herein.

II. Alternative Exemplary Electrosurgical Forceps with Two-Stage Energy Activation As mentioned above, electrode trigger (142) is slidably coupled on the exterior of housing (132) such that the operator may actuate electrode trigger (142) with an available finger in order to provide RF energy to electrodes (113, 115) during exemplary use. In some instances, electrode trigger (142) may make electrode activation assembly (140) difficult or awkward to use. As one example, electrode trigger (142) may take up an undesirable amount of space on the exterior of housing (132) such that the operator may accidentally actuate electrode trigger (142). As another example, electrode trigger (142) may be placed at a location along housing (132) such that the operator may have difficulty reaching trigger (142) while sufficiently grasping tissue in accordance with the description herein.

As also mentioned above, resilient arm (134) may flex toward housing (132) when jaws (112, 114) are in the closed position to provide greater closure forces between jaws (112, 114). The closure forces provided by flexing resilient arm (134) may help activated electrodes (113, 115) properly seal tissue grasped between jaws (112, 114). During exemplary use, if the operator fails to generate enough closure force while jaws (112, 114) are in the closed position, electrodes (113, 115) may fail to properly seal tissue grasped between jaws (112, 114).

It may be desirable to provide an activation assembly configured to activate electrodes (113, 115) without the use of an independently actuated electrode trigger (142). It may be desirable to have an energy activation button that would be activated whenever the operator pivots resilient arm (134) to the position associated with jaws (212, 214) clamping tissue sufficient closure force to proper seal tissue grasped between jaws (212, 214). Further, it may be desirable to have an activation assembly configured to provide tactile response to the operator that further pivoting of resilient arm (134) will activate electrodes (213, 215), as well as a second tactile response to the operator that indicates resilient arm (134) has indeed activated electrode (213, 215).

While various examples of RF activation assemblies are described below, it should be understood various combinations or modifications may be made to such RF activation assemblies as would be apparent to one having ordinary skill in the art in view of the teachings herein.

Figure 5:
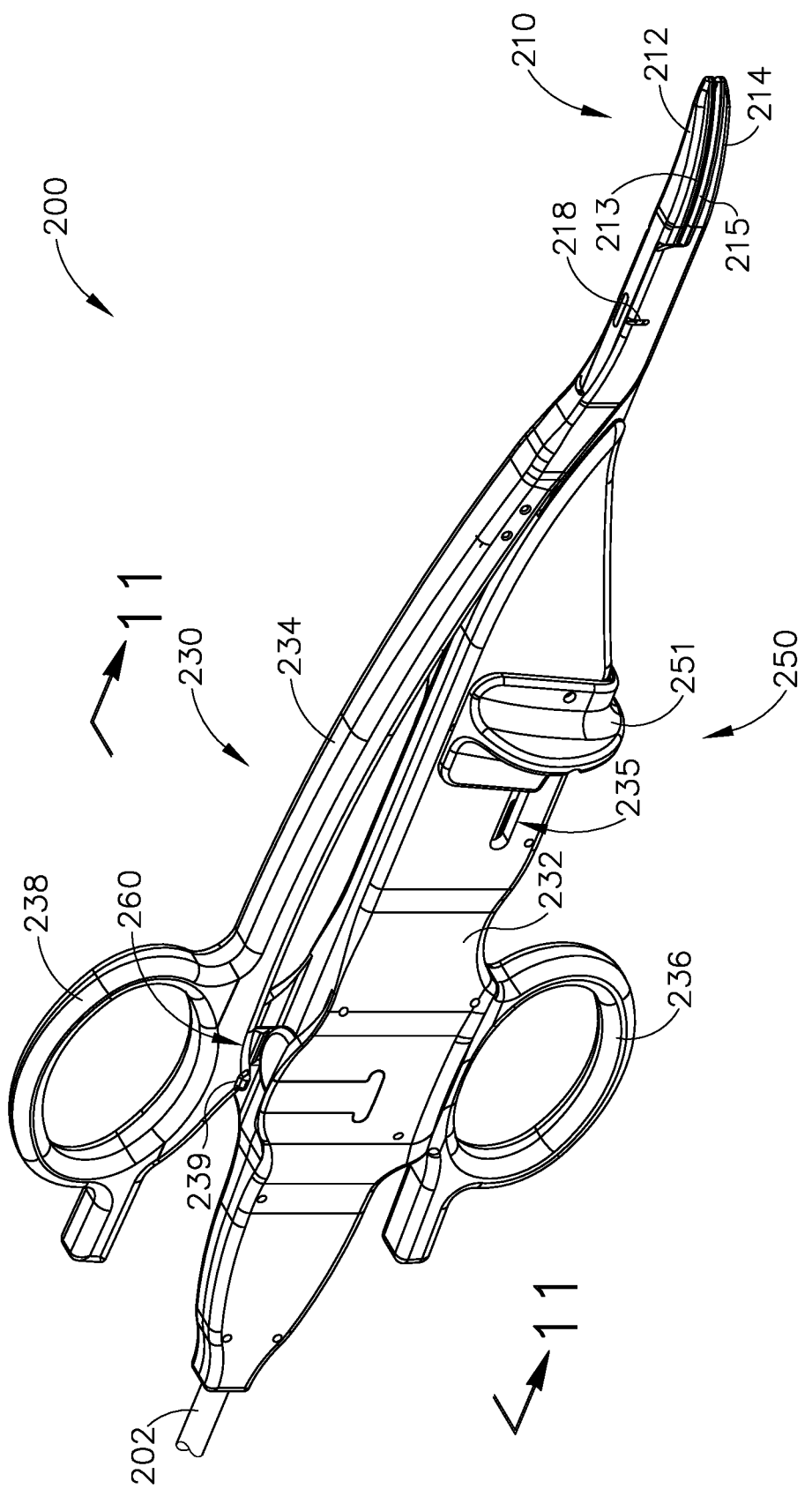
FIG. 5 depicts a perspective view of another exemplary electrosurgical forceps instrument, where an end effector is in a closed position, and where a resilient arm is in a relaxed position.

FIG. 5 shows an alternative exemplary electrosurgical forceps instrument (200) that may be used in replacement of instrument (100) described above. Therefore, as will be described in greater detail below, instrument (200) may be used to grasp, seal, and sever tissue. Instrument (200) includes an end effector (210), a handle assembly (230), a firing assembly (250), and an electrode activation assembly (260). End effector (210) is substantially similar to end effector (110) described above, with differences elaborated below. End effector (210) includes a first jaw (212) having a first electrode (213), a second jaw (214) having a second electrode (215), and a knife (220) configured to translate through the first jaw (212) and the second jaw (214).

Figure 6:
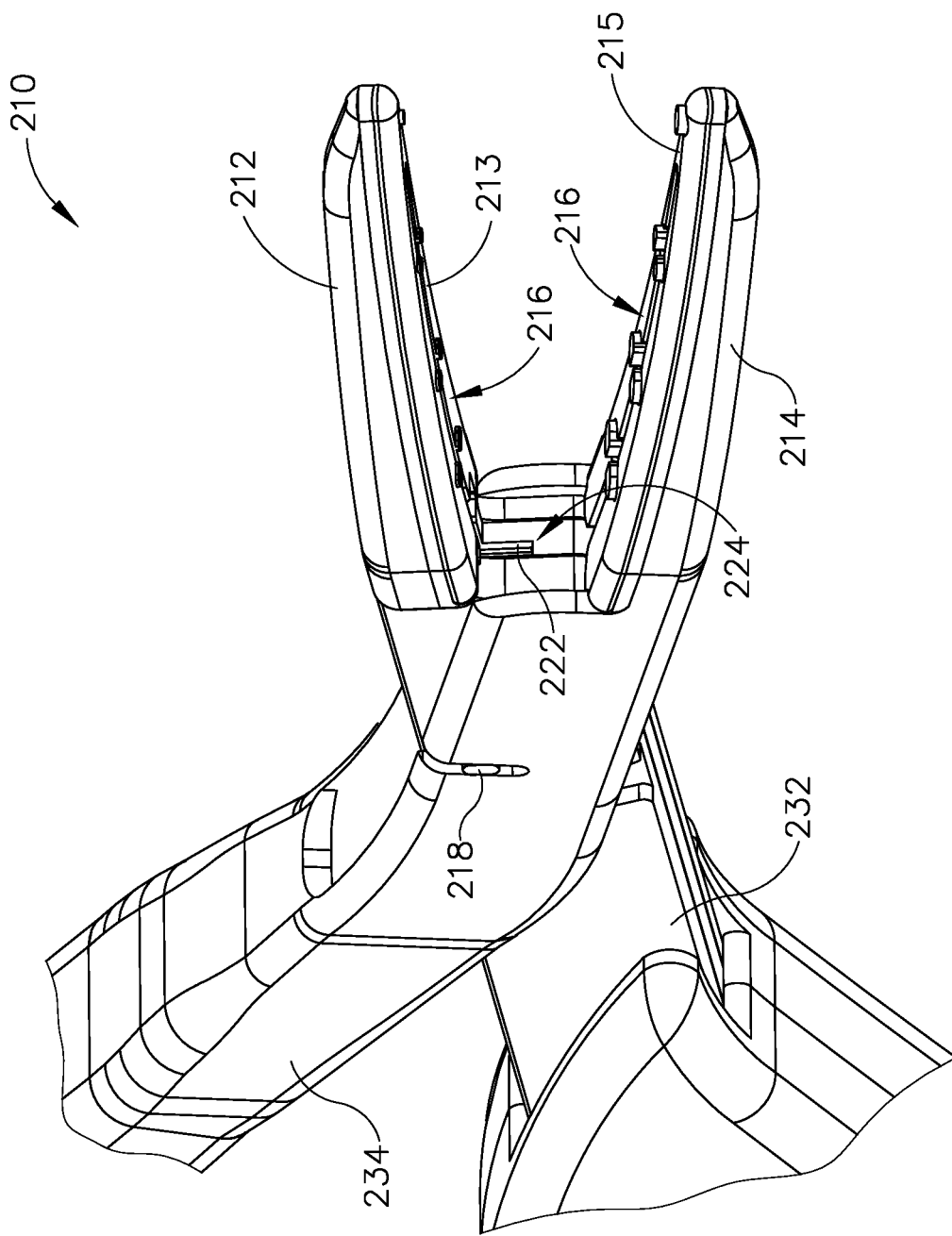
FIG. 6 depicts a perspective view of the end effector of FIG. 5 in an open position.
Figure 7:
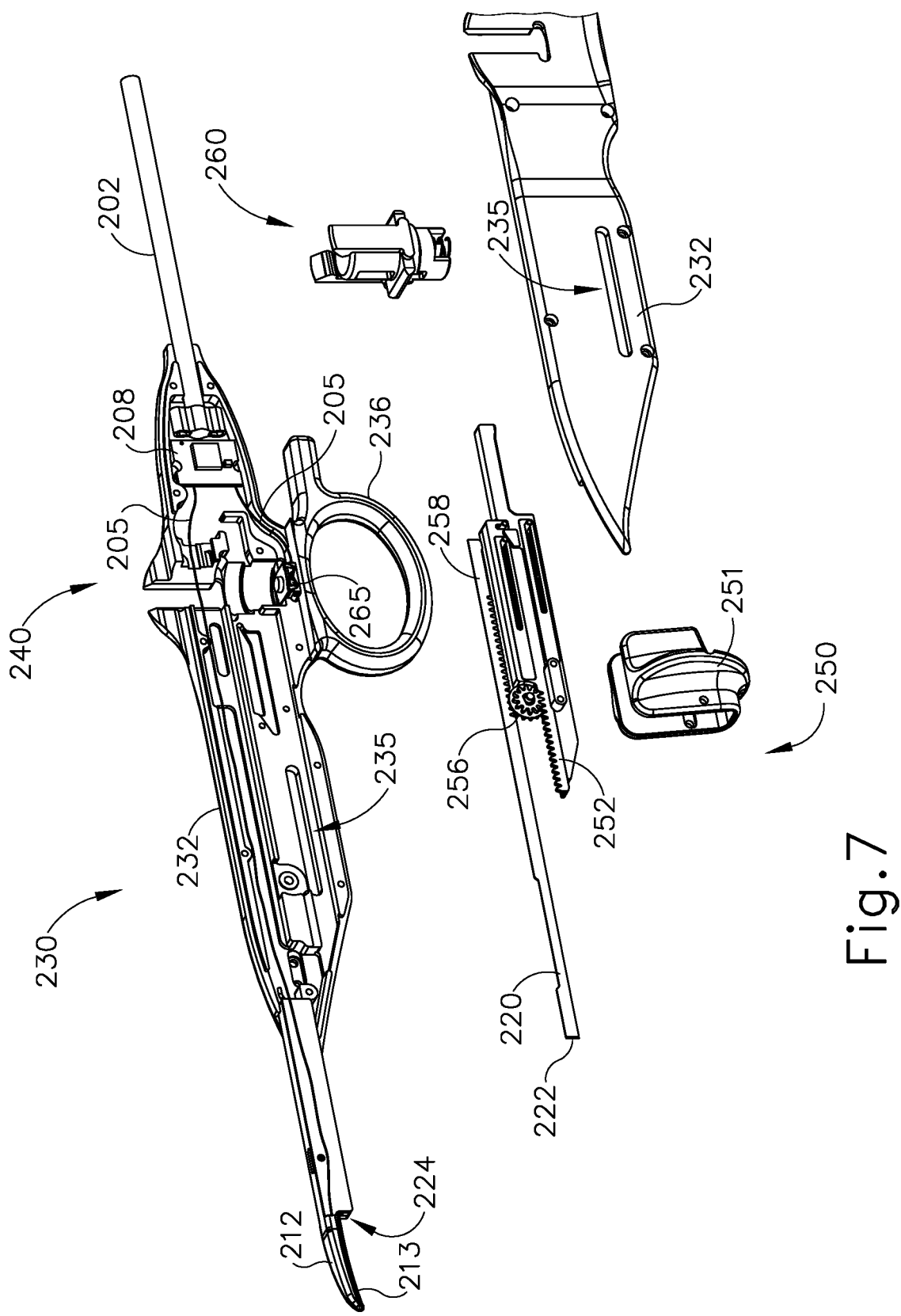
FIG. 7 depicts an exploded perspective view of a handle assembly of the instrument of FIG. 5.
Figure 10:
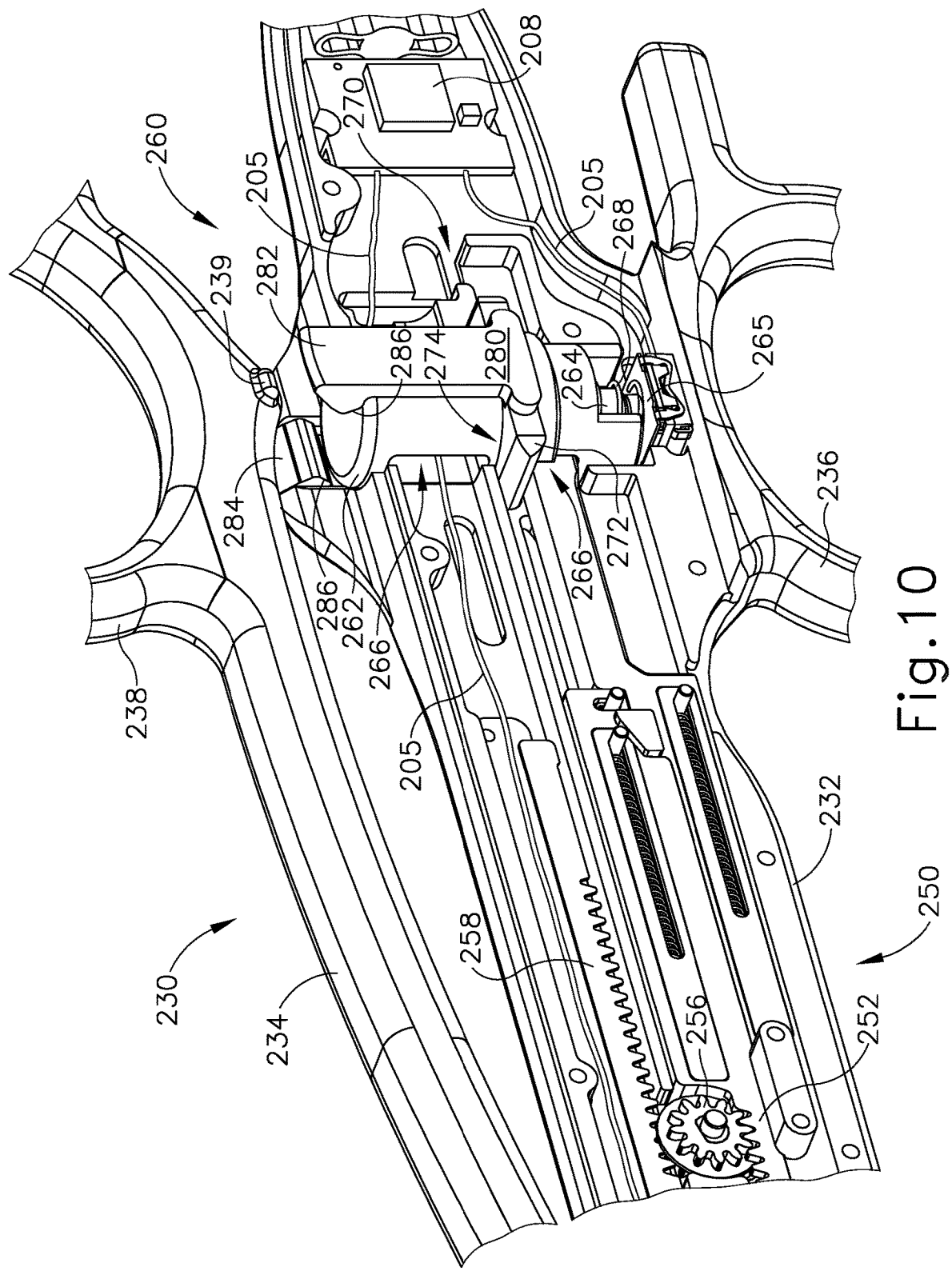
FIG. 10 depicts a perspective view of a portion of the instrument of FIG. 5, with a portion of the handle assembly of FIG. 7 omitted for clarity, where the resilient arm is in a relaxed position, where the activation assembly of FIG. 9 is in a deactivated configuration, wherein a thumb ring engagement assembly of the activation assembly is in a first position.

First jaw (212) and second jaw (214) are pivotably coupled with each other via pivot pin (218). First jaw (212) and second jaw (214) may pivot between an open position (FIG. 14A) and a closed position (FIG. 14B) in order to grasp tissue. First and second electrodes (213, 215) are positioned on respective jaws (212, 214) such that electrodes (213, 215) face each other when jaws (212, 214) are pivoted into the closed position. Additionally, each electrode (213, 215) is U-shaped in the present example, with the bend of the U-shape located near the distal end of each respective jaw (212, 214), such that each electrode (213, 215) includes two longitudinally extending, laterally spaced-apart legs extending along the length of each respective jaw (212, 214). Laterally spaced-apart legs of each electrode (213, 215) and corresponding portions of jaws (212, 214) define an elongate slot (216). Elongate slot (216) is dimensioned to slidably receive knife (220) such that knife may translate from a proximal position to a distal position, similar to knife (120) described above. As best shown in FIGS. 6 and 10, knife (220) includes a distal cutting edge (222) configured to sever tissue captured between jaws (212, 214) in the closed position.

A cable (202) extends proximally from handle assembly (230). Similar to cable (102) of instrument (100), cable (202) is configured to couple with control unit (104), which is further coupled with a power source (106). Therefore, control unit (104) is operable to provide RF power to electrodes (213, 215) of jaws (212, 214), to thereby seal tissue suitably captured between jaws (212, 214).

Handle assembly (230) includes a housing (232) and a resilient arm (234). Housing (232) and resilient arm (234) are substantially similar to housing (122) and resilient arm (134) described above, with differences elaborated below. Housing (232) and resilient arm (234) are pivotably coupled with each other via pivot pin (218). Housing (232) extends distally into first jaw (212), while resilient arm (234) extends distally into second jaw (214). Housing defines a knife pathway (224) that slidably houses a portion of knife (220). Housing (232) includes a finger ring (236) while resilient arm (234) terminates proximally into a thumb ring (238). Therefore, the operator may grasp instrument (200) in a scissor grip fashion and pivot resilient arm (234) relative to housing (232) via rings (236, 238) in order to open and close jaws (212, 214). Thumb ring (238) include a set of laterally presented detents (239).

Resilient arm (234) is sufficiently resilient such that arm (234) may flex from a relaxed position to a flexed position in response to pivoting arm (234) further toward housing (232) when jaws (212, 214) are already in the closed position (similar to resilient arm (134) shown in FIGS. 3B-3C). Resilient arm (234) is biased toward the relaxed position. Further pivoting of resilient arm (234) into the flexed position may result in greater closure forces between jaws (212, 214) as compared to pivoting jaws (212, 214) into the closed position while arm (234) is in the relaxed position. Resilient arm (234) may be suitably resilient such that when resilient arm (234) is pivoted into the flexed position, the closure force between jaws (212, 214) is sufficient such that electrodes (213, 215) may properly seal tissue grasped between jaws (212, 214). Additionally, the resilient nature of arm (234) may limit the amount of closure force between jaws (212, 214) such that jaws (212, 214) may not compress tissue too much, resulting in inadvertent tissue damage. When the operator no longer desires to compress tissue between jaws (212, 214) to properly seal or sever clamped tissue, the operator may reduce the amount of closure force applied to resilient arm (234) such that arm (234) returns to the relaxed position.

Housing (232) contains firing assembly (250) and electrode activation assembly (260). Firing assembly (250) is configured to actuate knife (220) between the proximal position and the distal position (Similar to knife (120) as shown in FIGS. 4A-4B) in response to proximal translation of knife trigger (251) within slot (235). Electrode activation assembly (260) is configured to selectively activate electrodes (213, 215).

As will be described in greater detail below, thumb ring (238) of resilient arm (234) and electrode activation assembly (260) are configured to activate electrodes (213, 215) when resilient arm (234) is in the flexed position. Additionally, laterally presented detents (239) of thumb ring (238) are dimensioned to interact with selected portions of activation assembly (260) which may help prevent accidental activation of electrodes (213, 215). Additionally, laterally presented detents (239) of thumb ring (238) may be dimensioned to interact with selected portions of activation assembly (260) in order to indicate to the operator that thumb ring (238) is directly adjacent to a translating body (262) of activation assembly (260) such that further flexing of resilient arm (234) may activate electrodes (213, 215). As will also be described in greater detail below, detents (239) may be configured to abut against selected portions of activation assembly (260) while resilient arm (234) is directly adjacent to translating body (262) in order to help reduce the force required to maintain resilient arm (234) in the flexed position.

Firing assembly (250) of the current example include a knife trigger (251) slidably coupled with housing (232) via slot (235), an input rack (252), a rotary drive assembly (256), and an output rack (258). Input rack (252) is slidably housed within housing (232). In particular, input rack (252) is associated with knife trigger (251) such that movement of knife trigger (251) in one direction may lead to movement of input rack (252) in the same direction. Rotary drive assembly (256) is rotatably coupled with housing (232) such that rotary drive assembly (256) may rotate relative to housing (232), but rotary drive assembly (256) may not translate relative to housing (232). Output rack (258) slidably housed within housing (232). In particular, output rack (258) is associated with knife (220) such that movement of output rack (258) drives movement of knife (220).

Figure 8A:
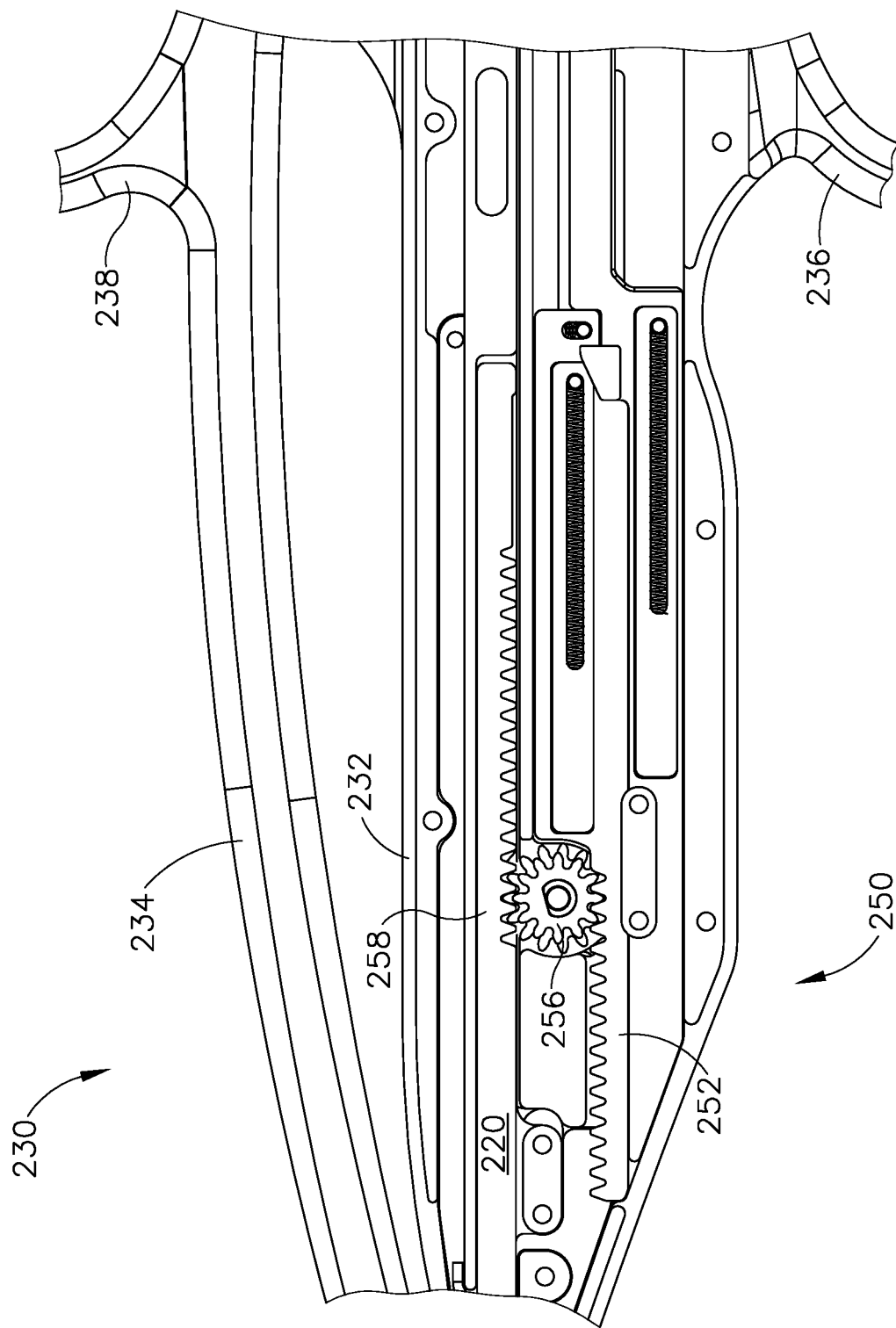
FIG. 8A depicts a side elevational view of the instrument of FIG. 5, with a portion of the handle assembly of FIG. 7 omitted for clarity, where a firing assembly is in a pre-fired position.
Figure 8B:
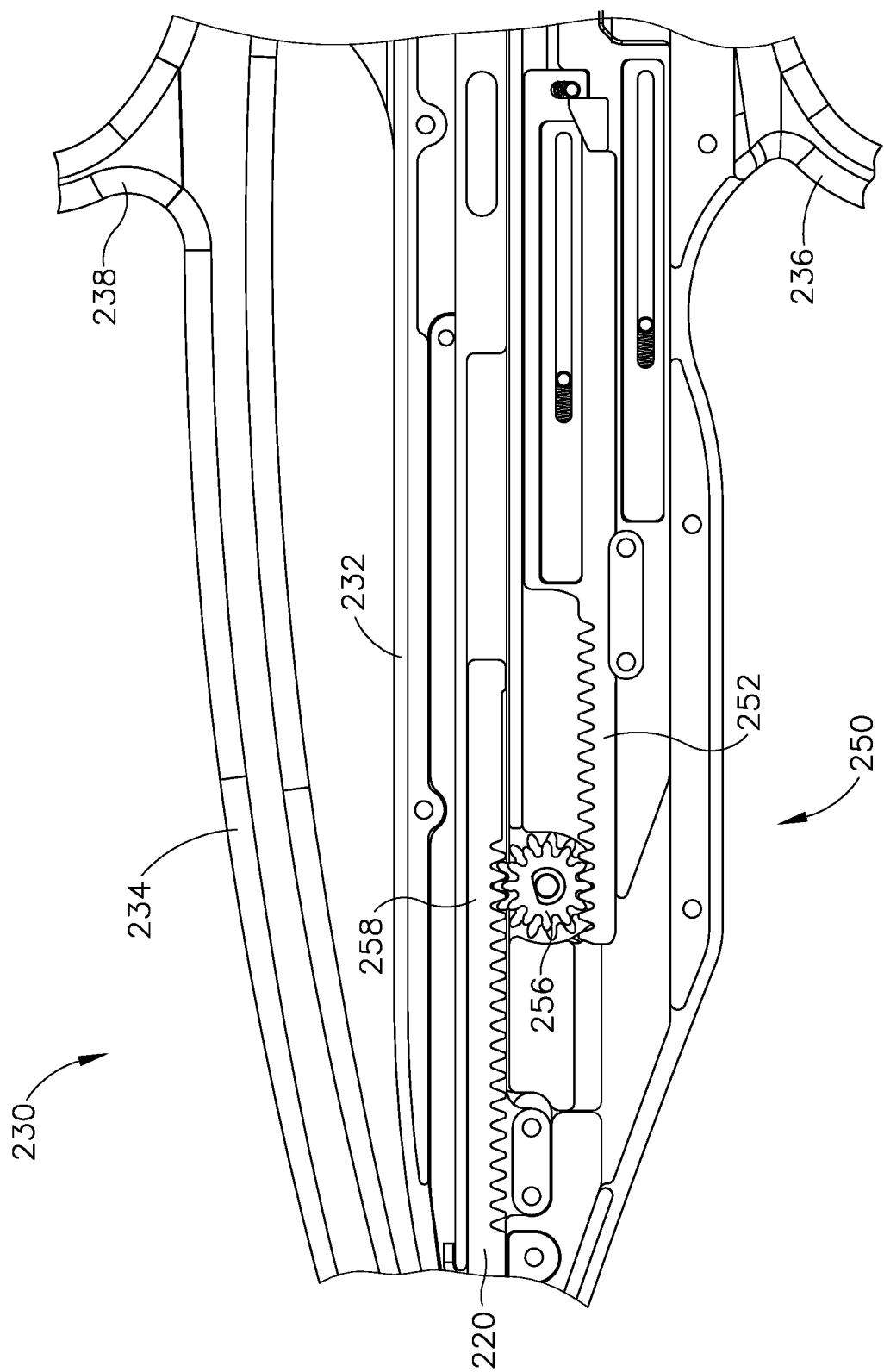
FIG. 8B depicts a side elevational view of the instrument of FIG. 5, with a portion of the handle assembly of FIG. 7 omitted for clarity, where the firing assembly of FIG. 8A is in a fired position.
Figure 9:
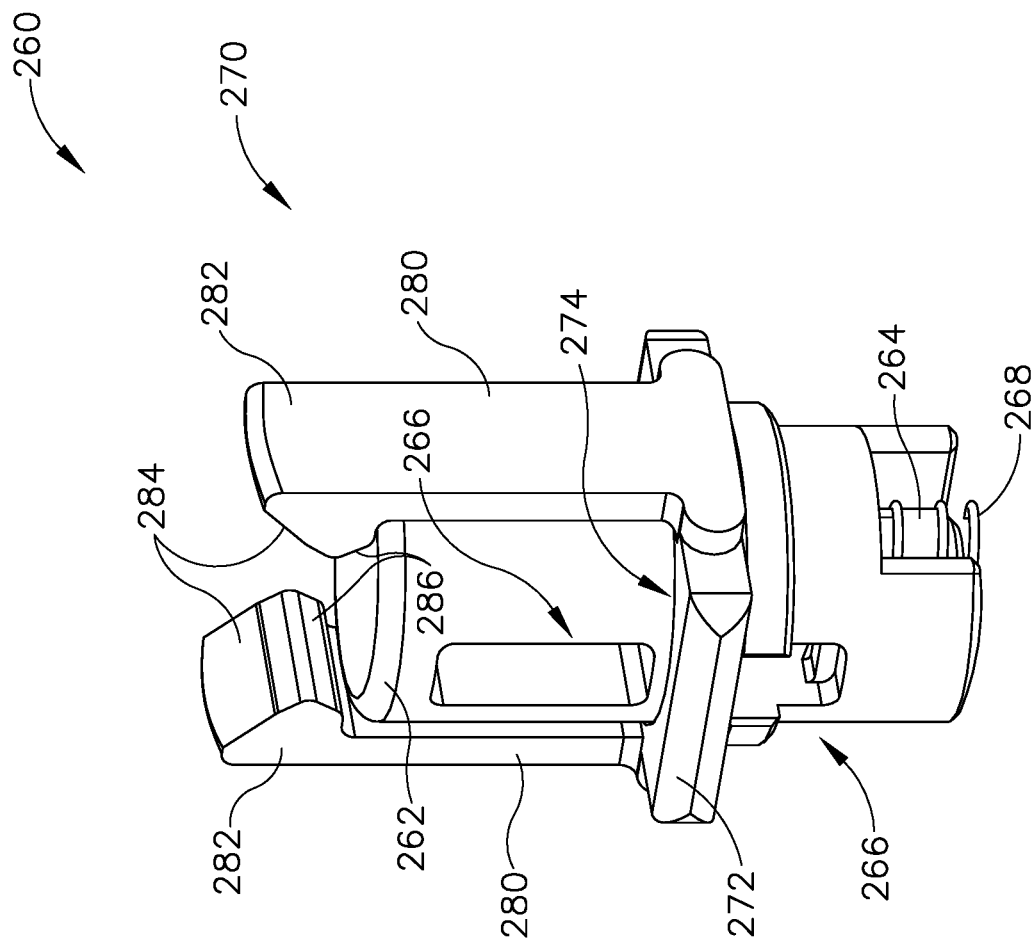
FIG. 9 depicts a perspective view of an activation assembly of the instrument of FIG. 5.

Input rack (252) meshes with a portion of rotary drive assembly (256), while output rack (258) also meshes with the opposite end of rotary drive assembly (256). FIG. 8A shows firing assembly (250) in a position associated with knife (220) being in the pre-fired position. If the operator desires to fire knife (220) through jaws (212, 214) while jaws (212, 214) are in the closed position in accordance with the description herein, the operator may proximally drive knife trigger (251) such that input rack (252) is also driven proximally. As shown in FIG. 8B, input rack (252) may rotate rotary drive assembly (256) in a first angular direction, causing rotary drive assembly (256) to actuate output rack (258) and knife (220) distally such that knife (220) actuates distally within jaws (212, 214) toward the fired position. In other words, proximally translation of knife trigger (251) is configured to distally fire knife (220). Knife trigger (251) or input rack (252) may be biased toward the distal position shown in FIG. 8A such that after the operator actuates knife trigger (251) proximally to fire knife (220), the operator may let go of knife trigger (251) such that input rack (252) rotates rotary drive assembly (256) in the second, opposite, angular direction, thereby driven output rack (258) and knife (220) proximally into the pre-fired position results in distal translation of knife (220).

While firing assembly (250) of the current example includes a rack and pinion configuration, any suitable firing assembly may be used in replacement of firing assembly (250) described above that would be apparent to one having ordinary skill in the art in view of the teachings herein.

As mentioned above, electrode activation assembly (260) is configured to selectively activate electrodes (213, 215). Electrode activation assembly (260) includes a translating body (262) contained within housing (232), a biasing member (268), a tactile activation button (265) fixed within the interior of housing (232), and a thumb ring engagement assembly (270).

Activation button (265) is in communication with a circuit board (208) via electrical coupling wires (205); while circuit board (208) is also in communication with at least one electrode (213, 215) via electrical coupling wires (205). In the present example, circuit board (208) is contained within housing (232). Circuit board (208) is in communication with cable (202) such that circuit board (208) and control unit (104) are in electrical communication with each other. Therefore, circuit board (208) is configured to transfer RF energy from control unit (104) to electrodes (213, 215). In particular, activation button (265) is configured to instruct circuit board (208) to transfer RF energy from control unit (104) to electrodes (213, 215) when buttons (265) are depressed. Tactile activation button (265) is also configured to provide a tactile response when depressed in order to indicate to the operator that RF energy is being transferred from control unit (104) to electrodes (213, 215). While in the current example, circuit board (208) acts as an intermediary between control unit (104), electrodes (213, 215), and button (265), this is merely optional, as button (265) and electrodes (213, 215) may be in communication with cable (202) and control unit (104) without the use of circuit board (208).

Figure 11A:
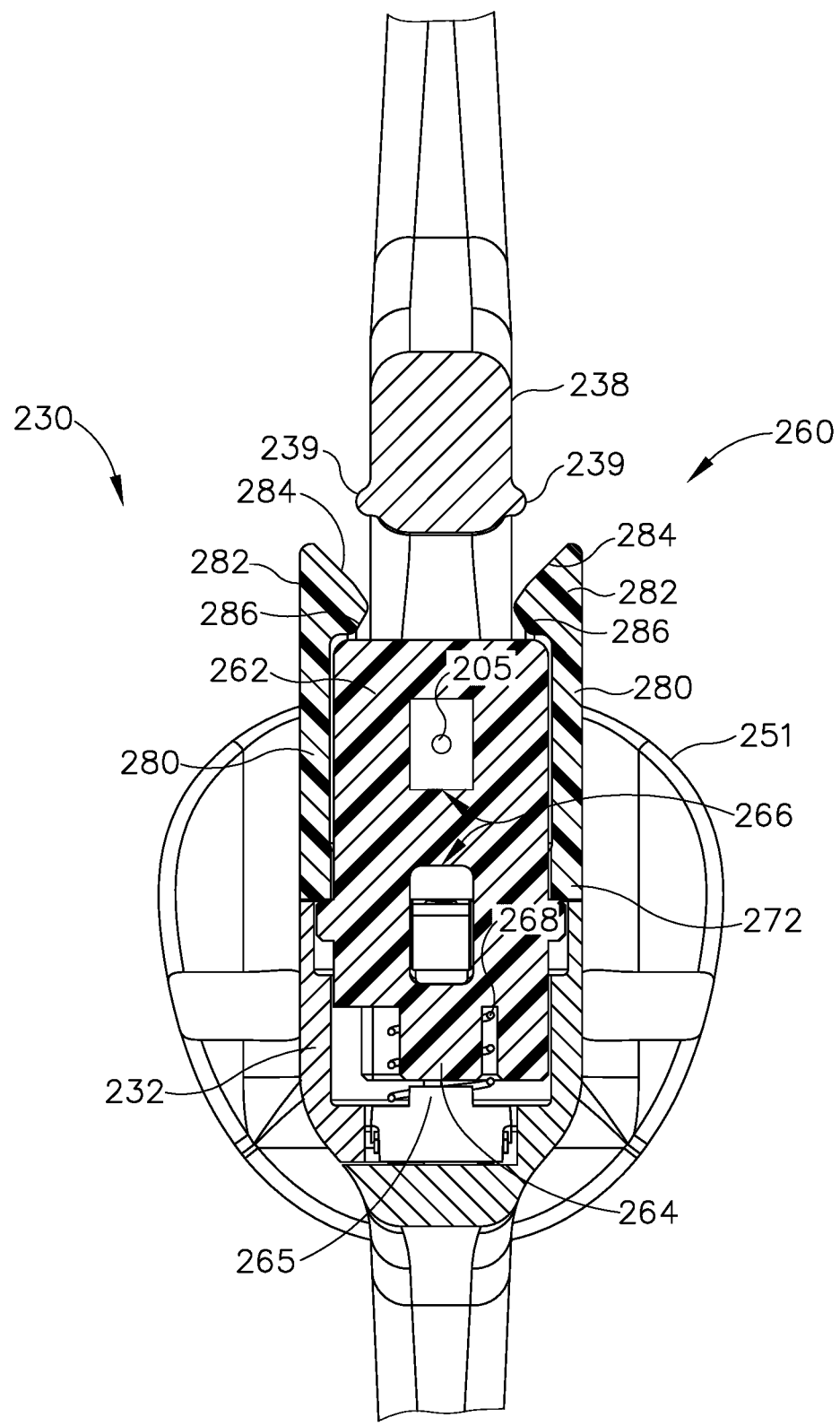
FIG. 11A depicts a cross-sectional view of the instrument of FIG. 5, taken along line 11-11 of FIG. 5, where the resilient arm is in a relaxed position, where the activation assembly of FIG. 9 is in the deactivated configuration, where the thumb ring engagement assembly of FIG. 10 is in the first position
Figure 11B:
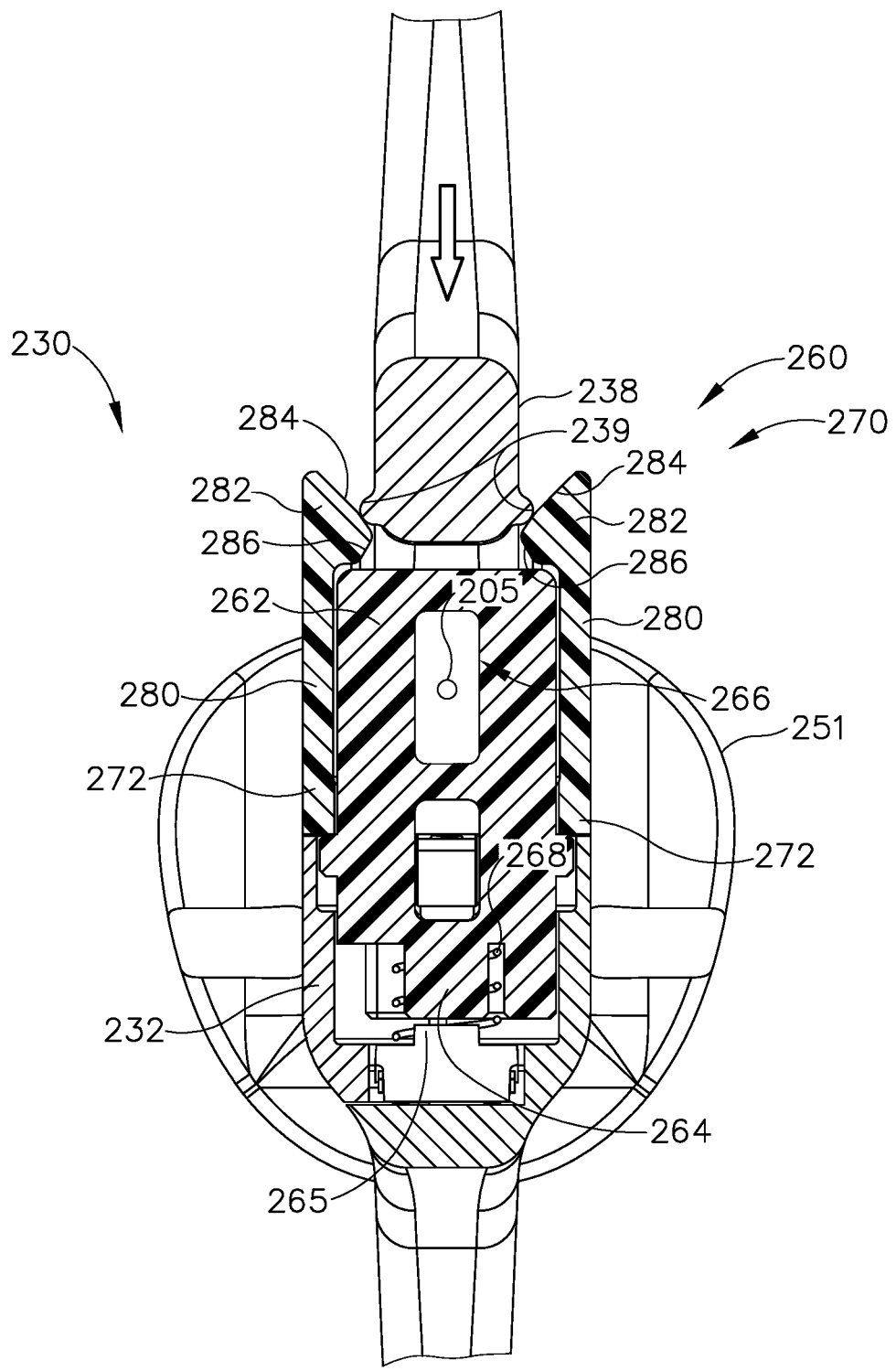
FIG. 11B depicts a cross-sectional view of the instrument of FIG. 5, taken along line 11-11 of FIG. 5, where the resilient arm is pivoted to initially contact the thumb ring engagement assembly of FIG. 10, where the activation assembly of FIG. 9 is in the deactivated configuration, where the thumb ring engagement assembly is in the first position.
Figure 11C:
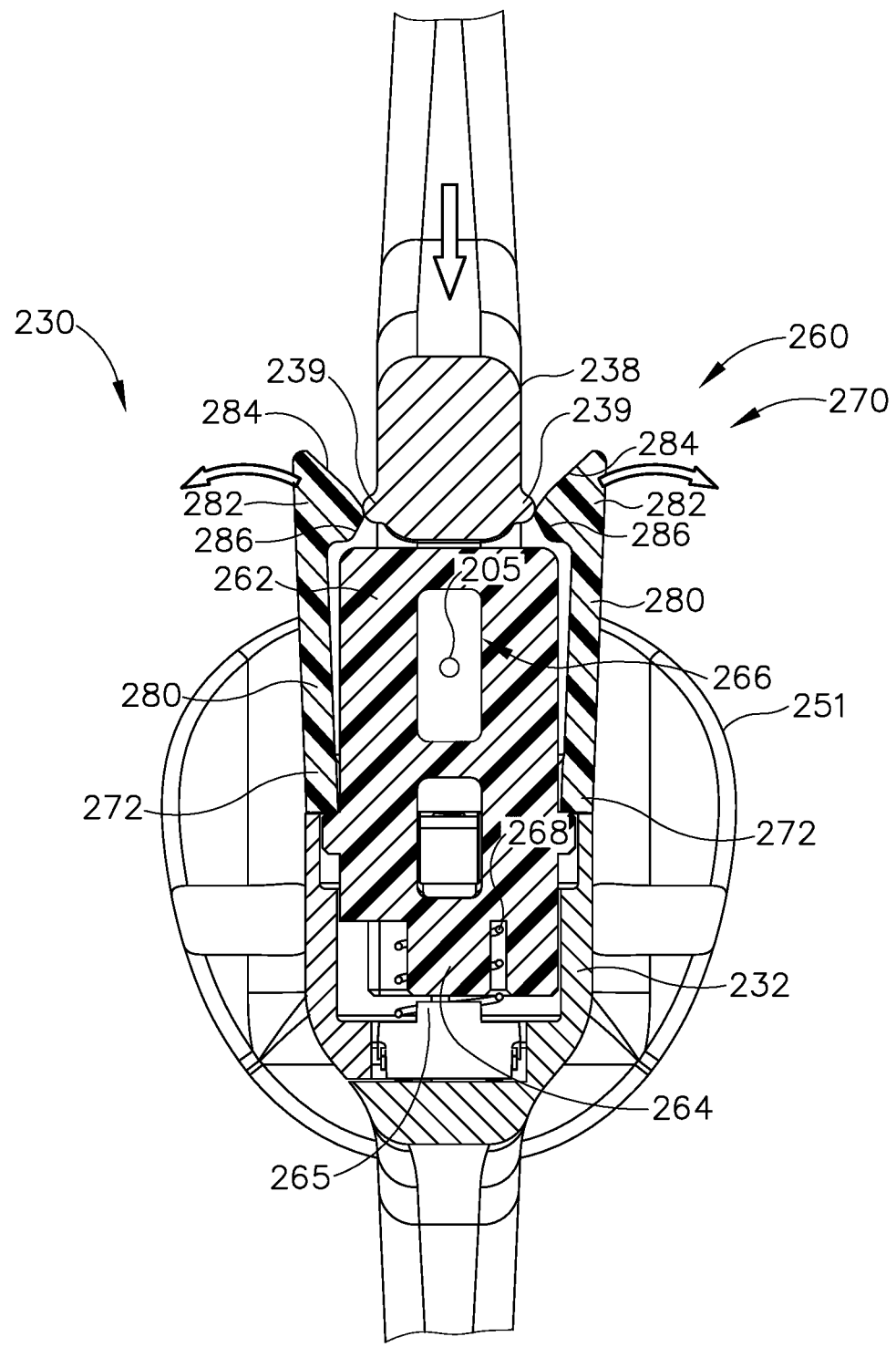
FIG. 11C depicts a cross-sectional view of the instrument of FIG. 5, taken along line 11-11 of FIG. 5, where the resilient arm is further pivoted into a flexed position, where the activation assembly of FIG. 9 is in the deactivated configuration, where the thumb ring engagement assembly of FIG. 10 is flexed into a second position.
Figure 11D:
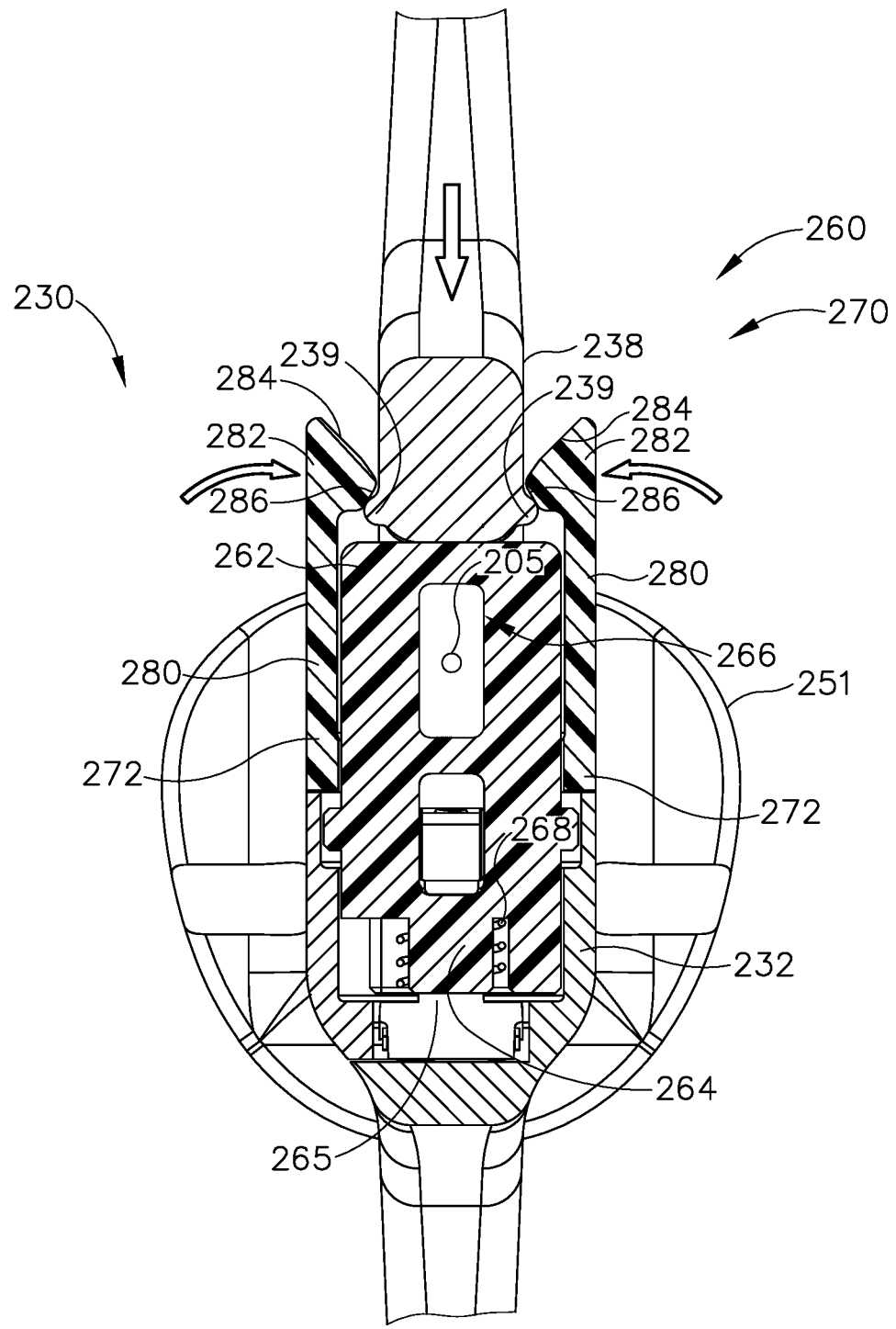
FIG. 11D depicts a cross-sectional view of the instrument of FIG. 5, taken along line 11-11 of FIG. 5, where the resilient arm is further pivoted in the flexed position into engagement with activation assembly of FIG. 9, where the activation assembly is in the deactivated configuration, where the thumb ring engagement assembly of FIG. 10 is in the first position.
Figure 11E:
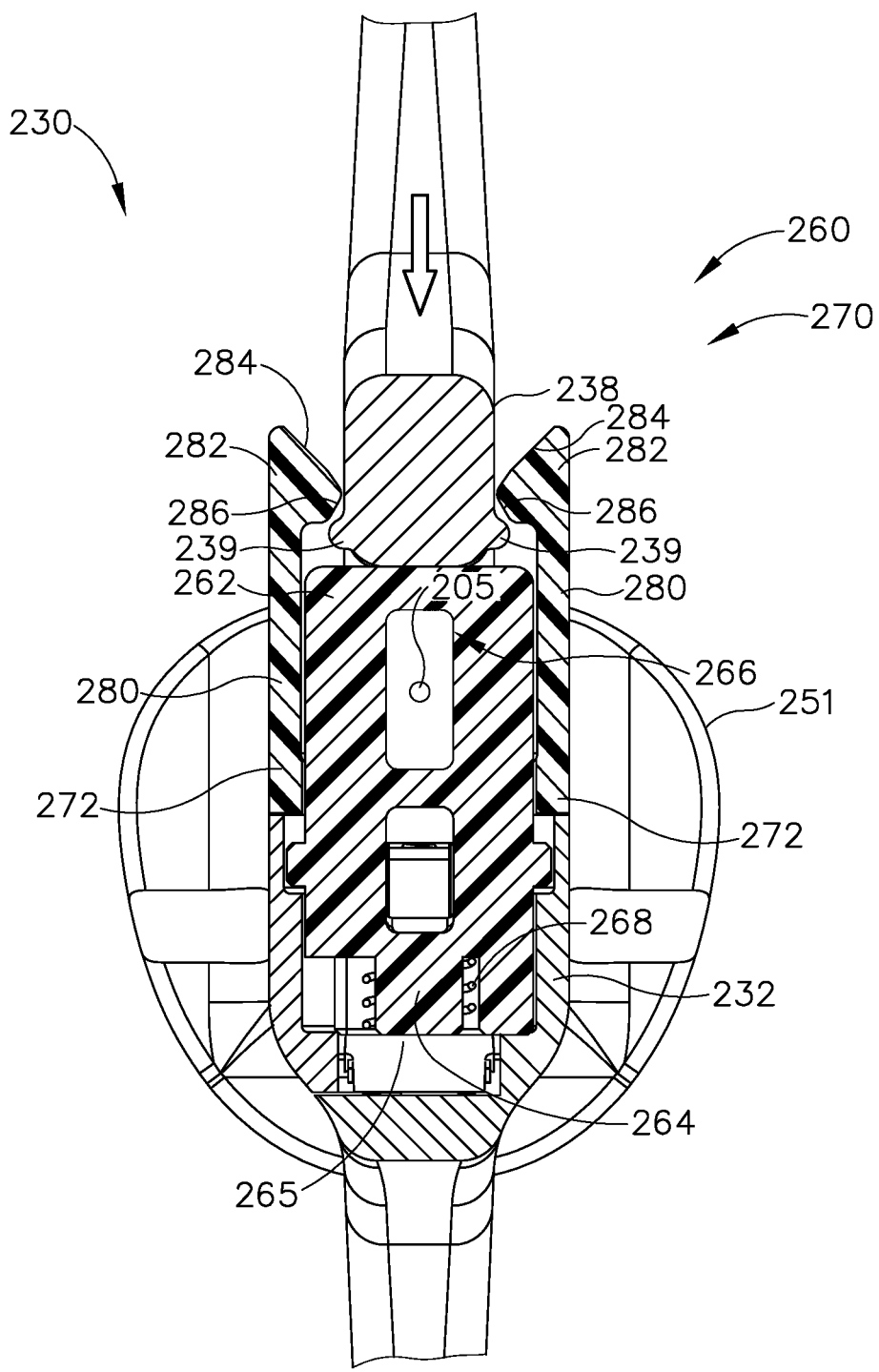
FIG. 11E depicts a cross-sectional view of the instrument of FIG. 5, taken along line 11-11 of FIG. 5, where the resilient arm is further pivoted in the flexed position into further engagement with the activation assembly of FIG. 9, where the activation assembly is in the activated configuration, where the thumb ring engagement assembly of FIG. 10 is in the first position.

Translating body (262) is slidably contained within housing (232) between a deactivated position (as shown in FIG. 10) and an activated position (as shown in FIG. 11E). Translating body (262) includes a downward protrusion (264) configured to sufficiently depress tactile activation button (265) to activate electrodes (213, 215) while translating body is in the activated position. It should be understood that downward protrusion (264) does not depress tactile activation button (265) when translating body (262) is in the deactivated position. Therefore, electrodes (213, 215) are activated when translating body (262) is in the activated position; and electrodes (213, 215) are deactivated when translating body (262) is in the deactivated position. Activation assembly (260) includes a biasing member (268) that biases translating body (262) into the deactivated position. Translating body (262) defines through holes (266) dimensioned to receive electrical coupling wires (205), any suitable moving parts or firing assembly (250), or any other suitable components as would be apparent to one having ordinary skill in the art in view of the teachings herein.

As best seen in FIG. 10, a portion of translating body (262) extends away from housing (232) toward thumb ring (238) while in the deactivated position. Thumb ring (238) is dimensioned to drive translating body (262) from the deactivated position into the activated position in response to flexing of resilient arm (234) while jaws (212, 214) are in the closed position. When thumb ring (238) drives translating body (262) into the activated position, depression of tactile activation button (265) emits a tactile feedback that may be felt by the operator, thereby indicating that electrodes (213, 215) are activated. Thumb ring (238) does not abut against the portion of translating body (292) extending away from housing (232) when resilient arm (234) is in the relaxed position, such that spring (298) biases translating body (262) into the deactivated position.

Therefore, the operator may pivot resilient arm (234) toward housing (232) while resilient arm (234) remains in the relaxed position to suitably grasp tissue between jaws (212, 214) without activating electrode (213, 215). Once the operator desires to activate electrodes (213, 215), the operator may further pivot resilient arm (234) toward housing (232) in order to flex resilient arm (234) such that thumb ring (238) drives translating body (262) into the activated position. With resilient arm (234) in the flexed position, the closure force between jaws (212, 214) is sufficient such that electrodes (213, 215) may suitably seal tissue grasped between jaws. Additionally, electrodes (213, 215) are activated since the flexing of resilient arm (234) allows thumb ring (238) to drive translating body (292) into the activated position, thereby depressing activation button (265). In other words, activation assembly (260) may be configured to activate electrodes (213, 215) when jaws (212, 214) provide a suitable closure force sufficient for electrodes (213, 215) to properly seal tissue grasped between jaws (212, 214).

In some examples, activation button (265) may not activate electrodes (213, 215), but may simply generate a single to control unit (104) indicating jaws (212, 214) are suitably closed. In such examples, control unit (104) may then further indicate to the operator that activation button (265) is activated through any suitable means as would be apparent to one having ordinary skill in the art in view of the teachings herein. For example, control unit (104) may emit an auditory tone in response to the signal generated by activation button (265). Control unit (104) may modify the auditory tone generated when electrodes (213, 215) are activated in response to receiving the signal generated by activation button (265). In such examples, an electrode activation assembly similar to electrode activation assembly (140) may be incorporated into instrument (200). In other words, activation button (265) may alternately act as part of an indictor assembly.

In addition or in the alternative to acting as part of an indicator assembly, activation button (265) may provide an electrical unlocking feature, enabling some other user input feature (e.g., something like RF trigger (142), etc.) to selectively activate electrodes (213, 215). For instance, such an RF-activating user input feature may be electrically locked out, and thereby rendered effectively inoperable to activate electrodes (213, 215), until activation button (265) is sufficiently actuated. After activation button (265) is sufficiently actuated, and for so long as activation button (265) is sufficiently actuated, the RF-activating user input feature may selectively activate electrodes (213, 215). After activation button (265) is no longer being sufficiently actuated, the RF-activating user input feature may be electrically locked out again, and thus again rendered effectively inoperable to activate electrodes (213, 215).

Thumb ring engagement assembly (270) includes a static base (272), two resilient bodies (280) extending upwardly from static base (272), and a cam body (282) located at the end of each resilient body (380). As will be described in greater detail below, thumb ring engagement assembly (270) is configured to engage detents (239) of thumb ring (238) in order to accidentally prevent the operator from accidentally activating electrodes (213, 215) while grasping tissue. Thumb ring engagement assembly (270) may also be configured to engage detents (239) in order to indicate to the operator that thumb ring (238) is directly adjacent to translating body (262) such that further flexing of resilient arm (242) may depress tactile activation button (265) to activate electrodes (213, 215). Additionally, as will be described in greater detail below, thumb ring engagement assembly (270) may abut against detents (239) after thumb ring (238) is positioned directly adjacent to translating body (262) in order to reduce the force required to keep resilient arm (232) in the flexed position during exemplary use.

Static base (272) is fixed within the interior of housing (232) when instrument (200) is assembled. Static base (272) defines a hole (274) that slidably receives a portion of translating body (262). Therefore, translating body (262) may actuate relative to static base (272) in accordance with the description herein. Resilient bodies (280) are connected to and extend upwardly from static base (272). In a naturally resting position, resilient bodies (280) extend substantially parallel with corresponding portions of translating body (262), however this is merely optional. Resilient bodies (280) may flex relative to static base (272) away from translating body (262) from the naturally resting position to an outwardly extending position in response to an external force. Resilient bodies (280) are sufficiently flexible that resilient bodies may return to the naturally resting position when an external force is no longer present.

Each resilient body (280) terminates into a respective cam body (282). While resilient bodies (280) extend adjacent to corresponding portions of translating body (262), cam bodies (282) are located above translating body (262). Cam bodies (282) each include a first cam surface (284) and a second cam surface (286). As will be described in greater detail below, laterally presented detents (239) are dimensioned to engage first cam surface (284) as thumb ring (238) moves toward activating translating body (262); while laterally presented detents (238) are dimensioned to engage second cam surface (286) as thumb ring (238) moves away from translating body (262). During exemplary use, engagement between first cam surface (284) and detents (239) may force the operator to push down on resilient arm (234) and/or thumb ring (238) with a sufficient force to move thumb ring (238) past first cam surface (284) to a position directly adjacent to translating body; as well as provide tactile feedback that further movement of thumb ring (238) toward translating body (262) will activate electrodes (213, 215). Also during exemplary use, engagement between second cam surface (286) and detents (238) may reduce the closure force required for the operator to maintain resilient arm (234) in the flexed position while being directly adjacent to translating body (262) in the deactivated position.

FIGS. 11A-11G show an exemplary use of activation assembly (260) in order to activate electrodes (213, 215) to seal tissue grasped between jaws (212, 214). FIG. 11A shows thumb ring (238) in a position corresponding with resilient arm (232) in the relaxed position (similar to that shown of resilient arm (134) in FIG. 3B). At this moment, jaws (212, 214) may be in the closed position suitably grasping tissue or substantially in the closed position. Thumb ring (238) is in a position such that detents (239) are above respective cam bodies (282). It should be understood that at this moment, translating body (262) is in the deactivated position such that electrodes (213, 215) are deactivated. In examples where activation button (265) generates a signal to control unit (104) when activated, translating body (262) is in the position where activation button (265) does not generate the signal.

Next, the operator may further pivot resilient arm (234) toward housing (232) such that thumb ring (238) is in the position shown in FIG. 11B. At this position, detents (239) initially contact first cam surface (284) such that resilient bodies (280) remain in the naturally resting position. At this moment, arm (234) may have initially begun to flex or may be in the relaxed position such that any further movement toward housing (232) would cause arm (234) to flex. Again, translating body (262) remains in the deactivated position such that electrodes (213, 215) remain deactivated. In examples where activation button (265) generates a signal to control unit (104) when activated, translating body (262) is in the position where activation button (265) does not generate the signal.

Next, the operator may further pivot resilient arm (234) toward housing (232) such that thumb ring (238) is in the position shown in FIG. 11C. At this position, detents (239) engage first cam surface (284) such that resilient bodies (280) flex away from both translating body (262) and thumb ring (238). At this moment, resilient arm (234) is in a flexed position such that the resilient nature of arm (234) urges arm (234) toward the relaxed position where thumb ring (238) is further away from translating body (262). However, the operator is pressing downwardly on arm (234) or thumb ring (238) with sufficient force to overcome the resilient nature of arm (234) as well overcome to force required to flex resilient bodies (280) away from both translating body (262) and thumb ring (238). Again, translating body (262) still remains in the deactivated position such that electrodes (213, 215) remain deactivated. In examples where activation button (265) generates a signal to control unit (104) when activated, translating body (262) is in the position where activation button (265) does not generate the signal.

Next, the operator may further pivot resilient arm (234) toward housing (232) such that thumb ring (238) is in the position shown in FIG. 11D. At this position, Thumb ring (238) has partially actuated translating body (262) such that downward protrusion (264) is about to fully depress tactile activation button (265). Also, detents (239) have cleared first cam surface (284) such that resilient bodies (280) return to the naturally resting position. When resilient bodies (280) return to the natural resting position, cam bodies (282) may snap against thumb ring (238) providing tactile feedback to the operator. Therefore, the operator may be aware that detents (239) cleared first cam surfaces (284). The operator may also be aware that any further pivoting of resilient arm (234) towards housing (232) may activate electrodes (213, 215) by depressing activation button (265).

In examples where activation button (265) generates a signal to control unit (104) when activated, the operator may be aware that any further pivoting of resilient arm (234) towards housing (232) may cause activation button (265) to generate the signal to control unit (104). In some examples, activation button (265) may be entirely omitted such that an electrode activation assembly similar to electrode activation assembly (140) is incorporated. In such instances, the tactile feedback provided by the snapping back of resilient bodies (280) when detents (239) clear first cam surface (284) may indicate to the operator that jaws (212, 214) are suitably closed such that activation of electrode (213, 215) may properly seal tissue captured between jaws (212, 214).

Additionally, at the moment shown in FIG. 11D, resilient arm (234) is in the flexed position such that the resilient nature of arm (234) urges arm (234) toward the relaxed position where thumb ring (238) is further away from translating body (262). However, the operator may press downward on arm (234) or thumb ring (238) with sufficient force to overcome the resilient nature of arm (234), keeping arm (234) in the flexed position. After long periods of keeping resilient arm (234) in the flexed position, the operator may be come fatigued. However, detents (239) are in contact with second cam surface (286) such that the contact between detents (239) and second cam surface (286) may help support the operator in keeping resilient arm (234) in the flexed position. In other words, the contact between detents (239) and second cam surface (286) may reduce the amount of downward force required by the operator to keep arm (234) in the flexed position. The resilient nature of arm (234) may be strong enough to overcome the force provided by the contact between detents and second cam surface (286) such that if the operator let go of thumb ring (238), the resilient nature of arm (234) would force detents (239) to flex resilient bodies (280) outwardly such that resilient arm (234) would return to the natural position. In other words, the downward force provided by contact between detents (239) and second cam surface (286) may not be sufficient to keep resilient arm (234) in the flexed position all by itself.

Next, as shown in FIG. 11E, the operator may further flex resilient arm (234) such that thumb ring (238) drives translating body (262) to the activated position. Therefore, downward protrusion (264) fully depresses tactile activation button (265) such that electrodes (213, 215) are activated. Additionally, tactile activation button (265) transmits a tactile response to the operator in order to confirm activation of electrodes (213, 215). With resilient arm (234) in the flexed position, the closure force provided by jaws (212, 214) is also sufficient for suitably sealing tissue with activated electrodes (213, 215). The operator may hold thumb ring (238) down for a suitable time such that activated electrodes (213, 215) may seal tissue grasped between jaws (212, 214). In examples where activation button (265) generates a signal to control unit (104) when activated, translating body (262) is in the position where activation button (265) does generate the signal.

When the operator no longer desires to activate electrodes (213, 215), the operator may release all or some downward force on thumb ring (238) and/or resilient body (234) such that biasing member (268) pushes downward protrusion (264) of translating body (262) away from tactile activation button (265). Tactile activation button (265) may also provide a tactile response when button (265) is no longer being depressed such that the operator may be aware electrodes (213, 215) are no longer activated. The operator may slightly decrease the downward force provided on thumb ring (238) to return thumb ring (238) to the position shown in FIG. 11D, such that contact between detents (239) and second cam surface (286) help reduce the amount of downward force required to keep resilient arm (234) in the flexed position.

Figure 11F:
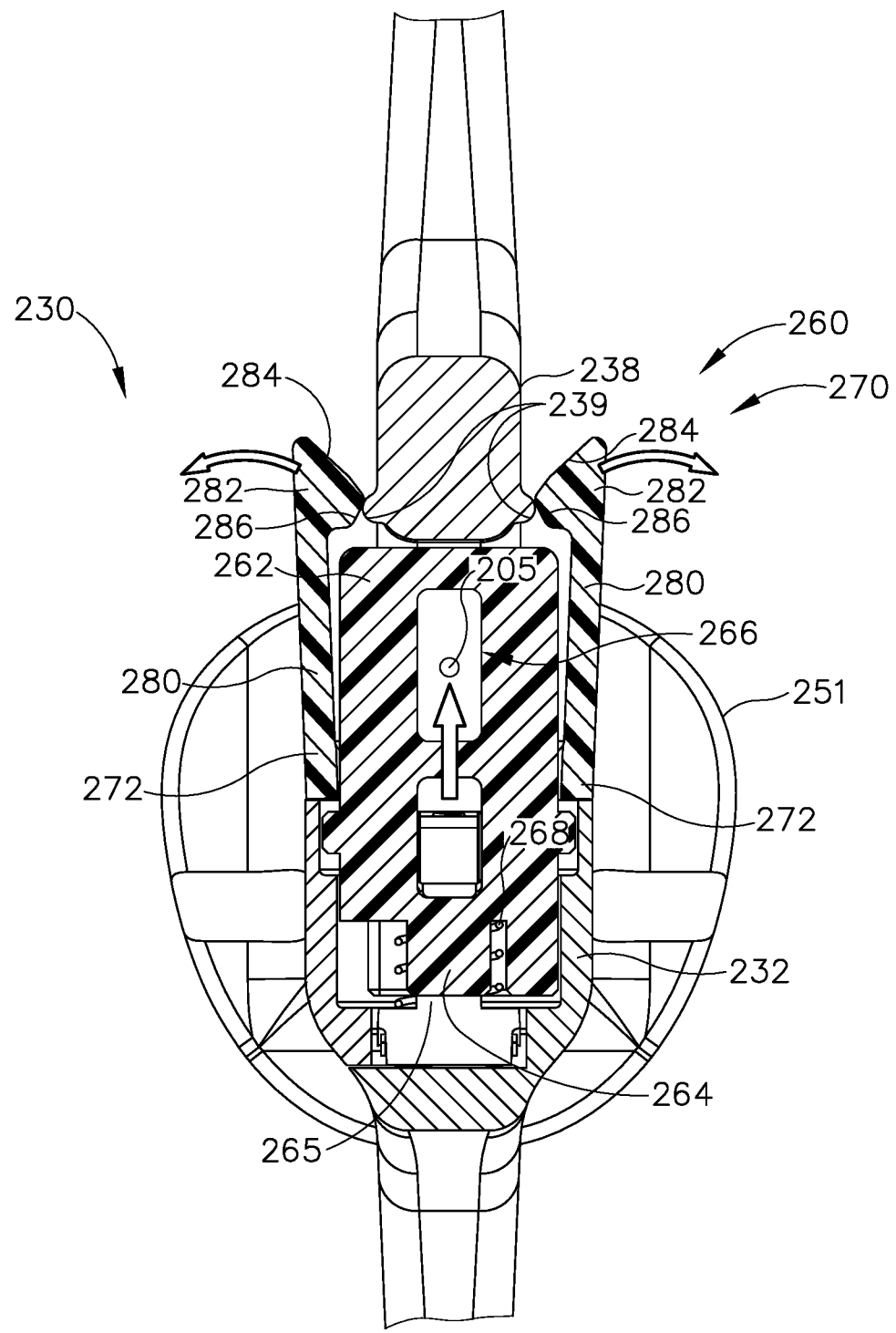
FIG. 11F depicts a cross-sectional view of the instrument of FIG. 5, taken along line 11-11 of FIG. 5, where the resilient arm is pivoted in the flexed position away from engagement with the activation assembly of FIG. 9, where the activation assembly is in the deactivated configuration, where the thumb ring engagement assembly of FIG. 10 is flexed into the second position.
Figure 11G:
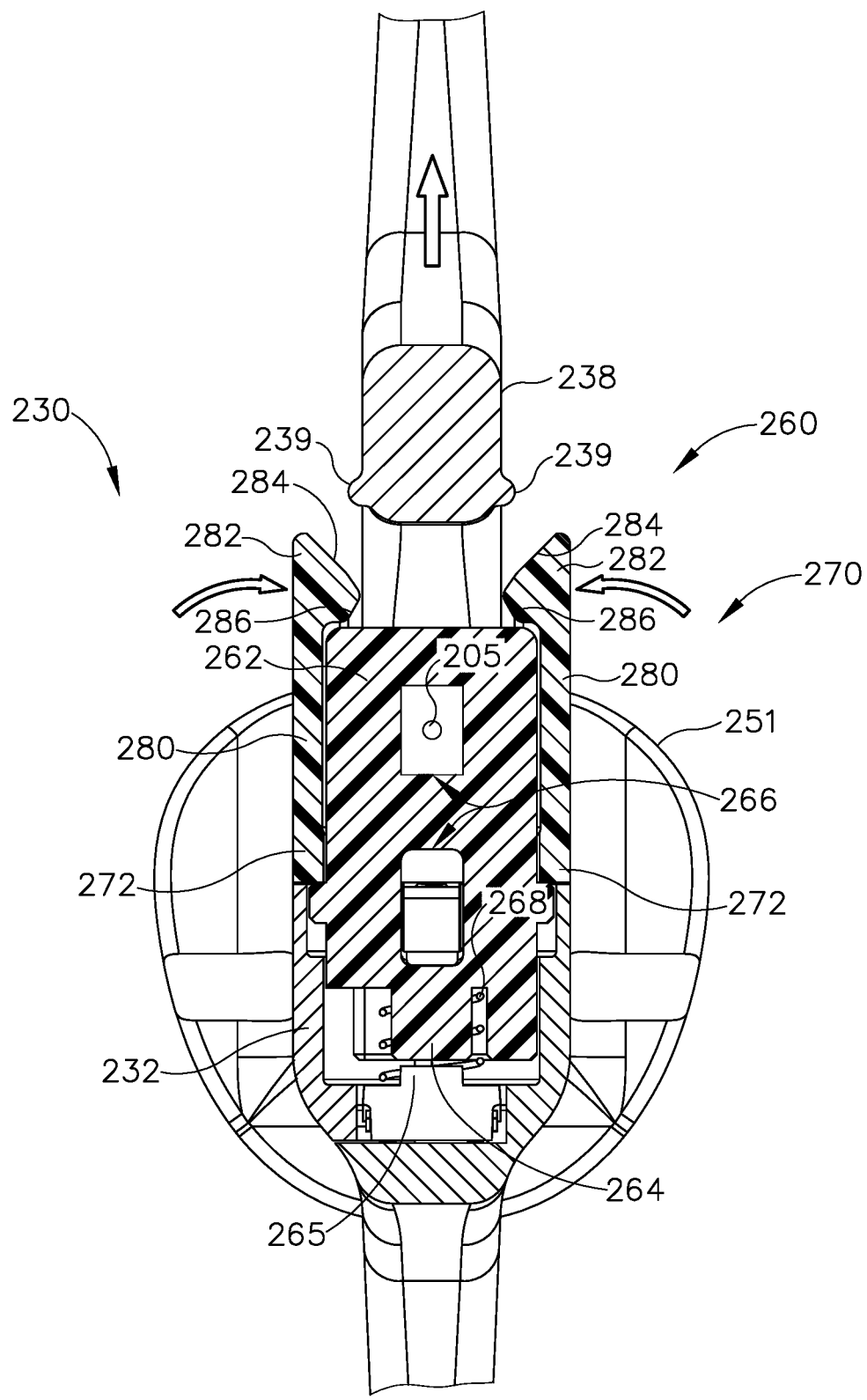
FIG. 11G depicts a cross-sectional view of the instrument of FIG. 5, taken along line 11-11 of FIG. 5, where the resilient arm is pivoted into the relaxed position away from engagement with the activation assembly of FIG. 9, where the activation assembly is in the deactivated configuration, where the thumb ring engagement assembly of FIG. 10 is in the first position.

Alternatively, as shown in FIG. 11F, the operator may decrease the downward force provided on thumb ring (238) such that the resilient nature of arm (234) urges arm (234) to the relaxed position, thereby pushing thumb ring (238) upward such that detents (239) slide along second cam surface (286) to flex resilient bodies (280) outwardly. As best shown in FIG. 11G, when detents (239) clear second cam surface (286), resilient bodies (280) may return to the natural relaxed position and thumb ring (238) may return to the position associated with resilient arm (234) in the relaxed position.

Figure 12:
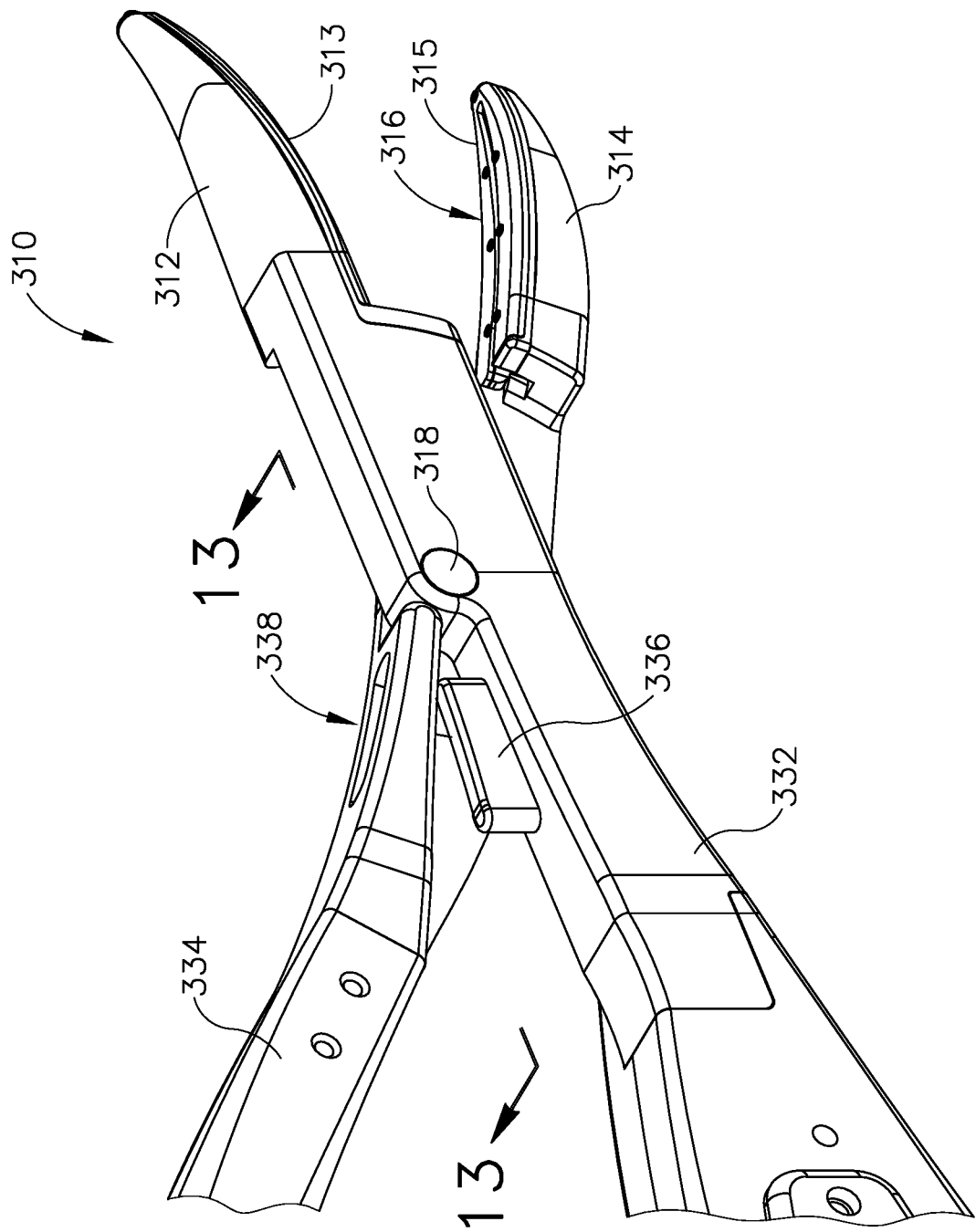
FIG. 12 depicts a perspective view of a distal portion of an alternative handle assembly and end effector that may be readily incorporated into the instrument of FIG. 5.
Figure 13A:
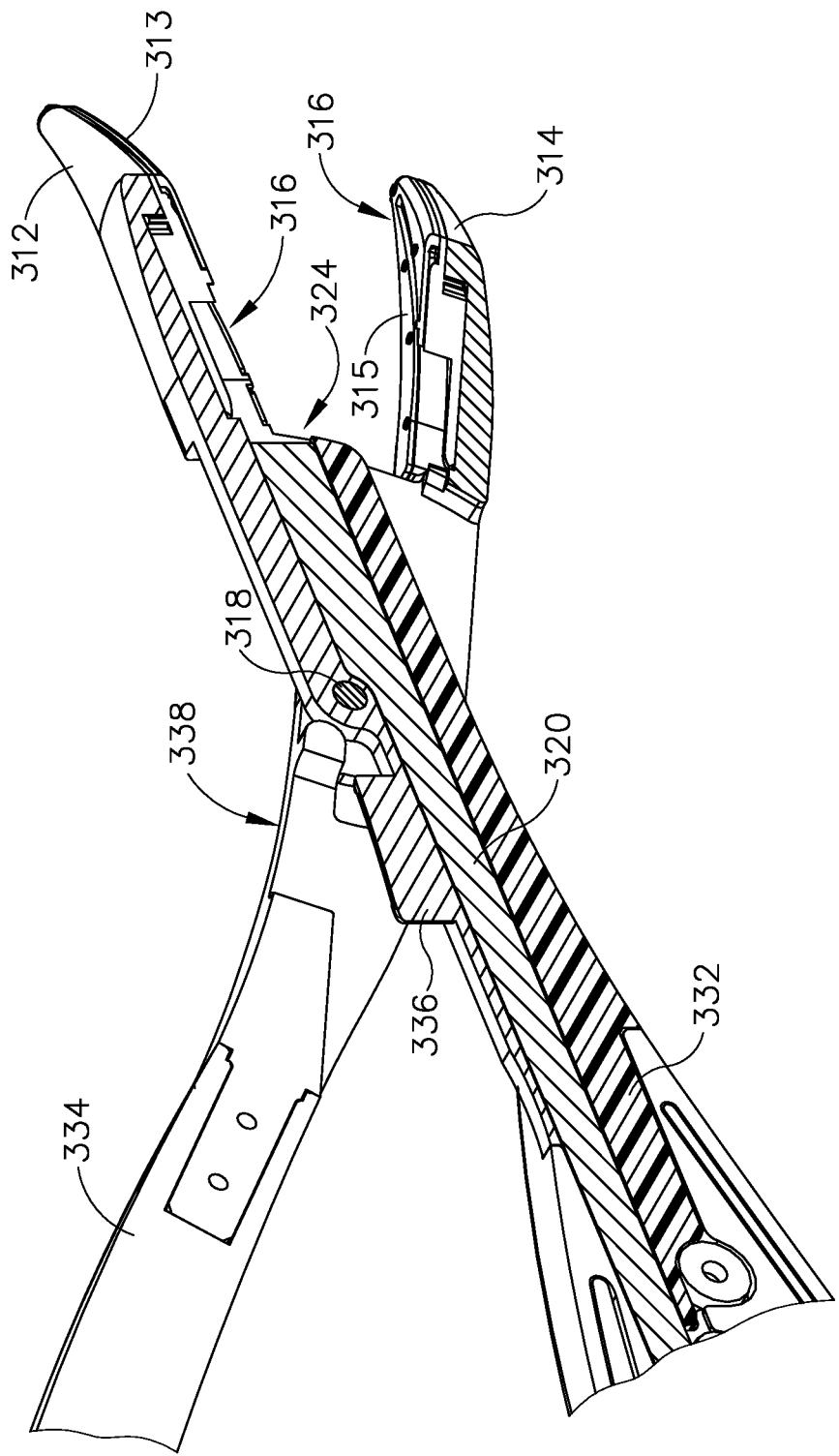
FIG. 13A depicts a cross-sectional perspective view of the distal portion of the handle assembly and end effector of FIG. 12, taken along line 13-13 of FIG. 12, where the end effector is in an opened configuration.
Figure 13B:
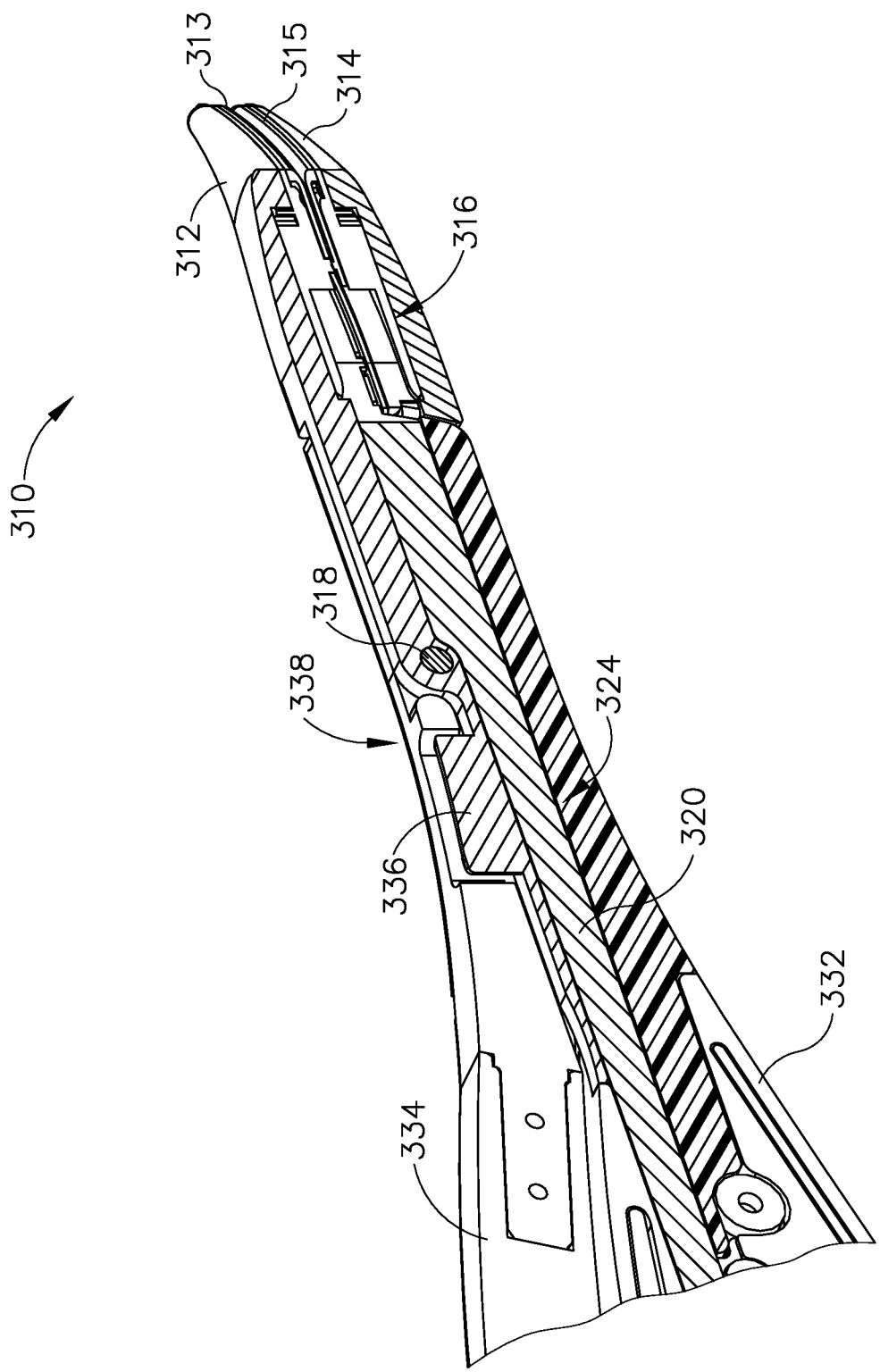
FIG. 13B depicts a cross-sectional perspective view of the distal portion of the handle assembly and end effector of FIG. 12, taken along line 13-13 of FIG. 12, where the end effector is in a closed configuration.

FIGS. 12-13B show an alternative end effector (310) that may be used in replaced of end effectors (110, 210) described above. End effector (310) is substantially similar to end effectors (110, 210) described above, with differences elaborated below. Therefore, end effector (310) includes a first jaw (312), a second jaw (314), a first electrode (313), a second electrode (315), a pivot pin (318), and knife (320); which are substantially similar to first jaw (212), second jaw (214), first electrode (213), second electrode (215), pivot pin (218), and knife (220) described above, respectively. Therefore, first electrode (313) and second electrode (315) define a pathway (316) configured to receive a knife (320). First jaw (312) extends proximally into housing (332) while second jaw (314) extends proximally into resilient arm (334).

Housing (332) and resilient arm (334) are substantially similar to housing (232) and resilient arm (234) described above, respectively, with differences elaborated below. In particular, housing (332) includes an upwardly extending protrusion (226) while resilient arm (334) defines a corresponding alignment cavity (338). As best seen in FIG. 13A-13B, upwardly extending protrusion (326) is dimension to fit within the confines of alignment cavity (338) when jaws (312, 314) are in the closed position in order to promote lateral alignment of jaws (312, 314) in the closed position.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) an end effector, wherein the end effector comprises: (i) a first jaw, (ii) a second jaw pivotably coupled with the first jaw, wherein the second jaw is operable to move between an open position and a closed position, (iii) a knife configured to actuate between a pre-fired position and a fired position, (iv) an electrode assembly configured to apply RF energy to tissue; (b) a handle assembly, wherein the handle assembly comprises: (i) a housing associated with the first jaw, and (ii) an arm associated with the second jaw, wherein the arm is configured to pivot the second jaw between the open position and the closed position, wherein the arm is configured to pivot relative to the housing between a first position, a second position, and a third position; and (c) an electrode activation assembly comprising: (i) an activation button associated with the handle assembly, wherein the activation button is configured to activate the electrode assembly in response to the arm pivoting to the third position, (ii) a resilient body comprising a first cam feature, and (iii) a detent associated with either the housing or the arm, wherein the detent is configured to engage the first cam feature as the arm pivots between the first position and the second position.

Example 2

The surgical instrument of Example 1, wherein the arm comprises a resilient member, wherein the resilient member is configured to transition between a relaxed configuration and a flexed configuration while the second jaw is in the closed configuration.

Example 3

The surgical instrument of Example 2, wherein the resilient member is configured to be in the flexed configuration in the second position and in the third position.

Example 4

The surgical instrument of any one or more of Examples 1 through 3, wherein the resilient body comprises a second cam feature.

Example 5

The surgical instrument of Example 4, wherein the detent is configured to abut against the second cam feature while the arm is in the second position.

Example 6

The surgical instrument of any one or more of Example 1 through 5, wherein the resilient body is coupled with the housing.

Example 7

The surgical instrument of Example 6, wherein detent is coupled with the arm.

Example 8

The surgical instrument of Example 7, wherein the arm further comprises a thumb ring, wherein the detent is coupled with the thumb ring.

Example 9

The surgical instrument of any one or more of Examples 1 through 8, wherein the activation button is configured to actuate relative to the resilient body.

Example 10

The surgical instrument of any one or more of Examples 1 through 9, wherein the activation button comprises a tactile button coupled with the housing and an actuating body slidably coupled with the housing.

Example 11

The surgical instrument of Example 10, wherein the actuating body defines a through hole.

Example 12

The surgical instrument of Example 11, further comprising an electrical wire coupled with the electrode assembly, wherein the electrical wire extends through the through hole defined by the actuating body.

Example 13

The surgical instrument of any one or more of Examples 1 through 12, wherein the resilient body is coupled to a static body fixed to the housing.

Example 14

The surgical instrument of Example 13, wherein the resilient body defines an opening, wherein the activation button is slidably disposed within the opening.

Example 15

The surgical instrument of any one or more of Examples 1 through 14, wherein the activation button comprises a resilient member biasing the activation button to a position associated with the electrodes being deactivated.

Example 16

A surgical instrument comprising: (a) an end effector, wherein the end effector comprises: (i) a first jaw, (ii) a second jaw pivotably coupled with the first jaw, wherein the second jaw is operable to move between an open position and a closed position, (iii) a knife configured to actuate between a pre-fired position and a fired position, (iv) an electrode assembly configured to apply RF energy to tissue; (b) a handle assembly, wherein the handle assembly comprises: (i) a housing associated with the first jaw, and (ii) an arm associated with the second jaw, wherein the arm is configured to pivot the second jaw between the open position and the closed position, wherein the arm is configured to pivot relative to the housing between a first position, a second position, and a third position; and (c) an arm engagement assembly comprising: (i) a resilient body comprising a first cam feature, and (ii) a detent associated with the arm, wherein the detent is configured to engage the first cam feature as the arm pivots between the first position and the second position.

Example 17

The surgical instrument of Example 16, wherein the detent is configured to drive the resilient body from a natural position to a flexed position while engaging the first cam feature, wherein the resilient body is configured to provide tactile feedback in response to the arm reaching the second position.

Example 18

The surgical instrument of any one or more of Examples 16 through 17, wherein the detent is configured to engage the first cam feature while the arm is in the second position, wherein the first cam feature and the detent are configured to resist the arm from pivoting toward the first position while engaged with each other.

Example 19

The surgical instrument of any one or more of Examples 16 through 18, further comprising an indicator assembly, where the arm in configured to transition between the second position and a third position, wherein the indictor assembly is configured to generate a signal in response to the arm reaching the third position.

Example 20

A surgical instrument comprising: (a) an end effector, wherein the end effector comprises: (i) a first jaw, (ii) a second jaw pivotably coupled with the first jaw, wherein the second jaw is operable to move between an open position and a closed position, (iii) a knife configured to actuate between a pre-fired position and a fired position, and (iv) an electrode assembly configured to apply RF energy to tissue; (b) a handle assembly, wherein the handle assembly comprises: (i) a housing associated with the first jaw, and (ii) an arm associated with the second jaw, wherein the arm is configured to pivot the second jaw between the open position and the closed position, wherein the arm is configured to pivot relative to the housing between a first position, a second position, and a third position; and (c) an electrode activation assembly comprising: (i) an activation button coupled with the housing, wherein the activation button is configured to activate the electrode assembly in response to the arm pivoting to the third position, (ii) an actuating body slidably coupled with the housing, wherein the actuating body is configured to trigger the activation button in response to the arm pivoting to the third position, (iii) a resilient body comprising a first cam feature and a second cam feature, wherein the resilient body is configured to move between a natural position and a flexed position, and (iv) a detent associated with the arm, wherein the detent is configured to engage the first cam feature as the arm pivots between the first position and the second position thereby driving the resilient body into the flexed position, wherein the resilient body is configured to move toward the natural position while the arm is in the third position.

IV. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Further, any one or more of the teachings, expressions, embodiments, examples, etc. described herein may be combined with any one or more of the teachings, expressions, embodiments, examples, etc. described in U.S. application Ser. No. 15/989,424, entitled "Method and Apparatus for Open Electrosurgical Shears," filed on May 25, 2018, published as U.S. Pub. No. 2019/0357962 on Nov. 28, 2019; U.S. application Ser. No. 15/989,430, entitled "Electrosurgical Shears with Knife Lock and Clamp-Actuated Switch," filed on May 25, 2018, issued as U.S. Pat. No. 10,966,781 on Apr. 6, 2021; U.S. application Ser. No. 15/989,433, entitled "Knife Drive Assembly for Electrosurgical Shears," filed on May 25, 2018, published as U.S. Pub. No. 2019/0357963 on Nov. 28, 2019; U.S. application Ser. No. 15/989,438, entitled "Knife Auto-Return Assembly for Electrosurgical Shears," filed on May 25, 2018, issued as U.S. Pat. No. 10,898,259 on Jan. 26, 2021; U.S. application Ser. No. 15/989,442, entitled "Compound Screw Knife Drive for Electrosurgical Shears," filed on May 25, 2018, issued as U.S. Pat. No. 10,856,931 on Dec. 8, 2020; U.S. application Ser. No. 15/989,448, entitled "Firing and Lockout Assembly for Knife for Electrosurgical Shears," filed on May 25, 2018, published as U.S. Pub. No. 2019/0357966 on Nov. 29, 2019; and U.S. application Ser. No. 15/989,455, entitled "Latching Clamp Arm for Electrosurgical Shears," filed on May 25, 2018, published as U.S. Pub. No. 2019/0357968 on Nov. 28, 2019. The disclosure of each of these applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A surgical instrument comprising:
   (a) an end effector, wherein the end effector comprises:
       (i) a first jaw,
       (ii) a second jaw pivotably coupled with the first jaw, wherein the second jaw is operable to move between an open position and a closed position,
       (iii) a knife configured to actuate between a pre-fired position and a fired position,
       (iv) an electrode assembly configured to apply RF energy to tissue;
   (b) a handle assembly, wherein the handle assembly comprises:
       (i) a housing associated with the first jaw, and
       (ii) an arm associated with the second jaw, wherein the arm is configured to pivot the second jaw between the open position and the closed position, wherein the arm is configured to pivot relative to the housing between a first position, a second position, and a third position; and
   (c) an electrode activation assembly comprising:
       (i) an activation button associated with the handle assembly, wherein the activation button is configured to activate the electrode assembly in response to the arm pivoting to the third position,
       (ii) a resilient body comprising a first cam feature, and
       (iii) a detent associated with either the housing or the arm, wherein the detent is configured to engage the first cam feature as the arm pivots between the first position and the second position.

2. The surgical instrument of claim 1, wherein the arm comprises a resilient member, wherein the resilient member is configured to transition between a relaxed configuration and a flexed configuration while the second jaw is in the closed position.

3. The surgical instrument of claim 2, wherein the resilient member is configured to be in the flexed configuration in the second position and in the third position.

4. The surgical instrument of claim 1, wherein the resilient body comprises a second cam feature.

5. The surgical instrument of claim 4, wherein the detent is configured to abut against the second cam feature while the arm is in the second position.

6. The surgical instrument of claim 1, wherein the resilient body is coupled with the housing.

7. The surgical instrument of claim 6, wherein the detent is coupled with the arm.

8. The surgical instrument of claim 7, wherein the arm further comprises a thumb ring, wherein the detent is coupled with the thumb ring.

9. The surgical instrument of claim 7, wherein the activation button is configured to actuate relative to the resilient body.

10. The surgical instrument of claim 1, wherein the activation button comprises a tactile button coupled with the housing and an actuating body slidably coupled with the housing.

11. The surgical instrument of claim 10, wherein the actuating body defines a through hole.

12. The surgical instrument of claim 11, further comprising an electrical wire coupled with the electrode assembly, wherein the electrical wire extends through the through hole defined by the actuating body.

13. The surgical instrument of claim 1, wherein the resilient body is coupled to a static body fixed to the housing.

14. The surgical instrument of claim 13, wherein the resilient body defines an opening, wherein the activation button is slidably disposed within the opening.

15. The surgical instrument of claim 1, wherein the activation button comprises a resilient member biasing the activation button to a position associated with the electrode assembly being deactivated.

16. A surgical instrument comprising:
    (a) an end effector, wherein the end effector comprises:
        (i) a first jaw,
        (ii) a second jaw pivotably coupled with the first jaw, wherein the second jaw is operable to move between an open position and a closed position,
        (iii) a knife configured to actuate between a pre-fired position and a fired position,
        (iv) an electrode assembly configured to apply RF energy to tissue;
    (b) a handle assembly, wherein the handle assembly comprises:

(i) a housing associated with the first jaw, and
(ii) an arm associated with the second jaw, wherein the arm is configured to pivot the second jaw between the open position and the closed position, wherein the arm is configured to pivot relative to the housing between a first position, a second position, and a third position; and (c) an activation assembly, comprising:
(i) an activation component coupled to the housing, wherein the activation component is configured to activate the electrodes in response to the arm pivoting into the third position,
(ii) a resilient body comprising a first cam feature, wherein the resilient body is configured to move between a natural position and a flexed position, and
(iii) a detent associated with the arm, wherein the detent is configured to engage the first cam feature as the arm pivots between the first position and the second position thereby driving the resilient body into the flexed position, wherein the resilient body is configured to move toward the natural position as the arm pivots toward the third position.

17. The surgical instrument of claim 16, wherein the resilient body is configured to provide tactile feedback in response to the arm reaching the second position from the first position.

18. The surgical instrument of claim 16, wherein the detent is configured to engage the first cam feature while the arm is in the second position, wherein the first cam feature and the detent are configured to resist the arm from pivoting toward the first position while engaged with each other.

19. The surgical instrument of claim 16, further comprising an indicator assembly, wherein the indictor assembly is configured to generate a signal in response to the arm reaching the third position.

20. A surgical instrument comprising:
(a) an end effector, wherein the end effector comprises:
(i) a first jaw,
(ii) a second jaw pivotably coupled with the first jaw, wherein the second jaw is operable to move between an open position and a closed position,
(iii) a knife configured to actuate between a pre-fired position and a fired position, and
(iv) an electrode assembly configured to apply RF energy to tissue;

(b) a handle assembly, wherein the handle assembly comprises:
(i) a housing associated with the first jaw, and
(ii) an arm associated with the second jaw, wherein the arm is configured to pivot the second jaw between the open position and the closed position, wherein the arm is configured to pivot relative to the housing between a first position, a second position, and a third position; and (c) an electrode activation assembly comprising:
(i) an activation button coupled with the housing, wherein the activation button is configured to activate the electrode assembly in response to the arm pivoting to the third position,
(ii) an actuating body slidably coupled with the housing, wherein the actuating body is configured to trigger the activation button in response to the arm pivoting to the third position,
(iii) a resilient body comprising a first cam feature and a second cam feature, wherein the resilient body is configured to move between a natural position and a flexed position, and
(iv) a detent associated with the arm, wherein the detent is configured to engage the first cam feature as the arm pivots between the first position and the second position thereby driving the resilient body into the flexed position, wherein the resilient body is configured to move toward the natural position while the arm is in the third position.

* * * * *